(12) United States Patent
Barman et al.

(10) Patent No.: US 8,470,800 B2
(45) Date of Patent: Jun. 25, 2013

(54) METHOD OF REDUCING INTRAOCULAR PRESSURE IN HUMANS

(75) Inventors: Shikha Barman, Bedford, MA (US); Rudolf A. Baumgartner, Sudbury, MA (US)

(73) Assignee: Inotek Pharmaceuticals Corporation, Lexington, MA (US)

( * ) Notice: Subject to any disclaimer, the term of this patent is extended or adjusted under 35 U.S.C. 154(b) by 395 days.

(21) Appl. No.: 12/771,289

(22) Filed: Apr. 30, 2010

(65) Prior Publication Data
US 2010/0279970 A1 Nov. 4, 2010

Related U.S. Application Data

(60) Provisional application No. 61/174,655, filed on May 1, 2009, provisional application No. 61/219,990, filed on Jun. 24, 2009.

(51) Int. Cl.
*A61K 31/70* (2006.01)
*C07H 19/167* (2006.01)
*C07H 19/173* (2006.01)

(52) U.S. Cl.
USPC .................. 514/46; 536/27.62; 536/27.63

(58) Field of Classification Search
None
See application file for complete search history.

(56) References Cited

FOREIGN PATENT DOCUMENTS
CN 101010085 8/2007
WO 2005/117910 A2 12/2005

OTHER PUBLICATIONS

U.S. Appl. No. 13/051,633, First Office Action on the Merits (FAOM), mailed May 17, 2012.*
U.S. Appl. No. 13/051,655, First Office Action on the Merits (FAOM), mailed May 16, 2012.*
U.S. Appl. No. 13/072,349, First Office Action on the Merits (FAOM), mailed Mar. 27, 2012.*
International Preliminary Report on Patentability and Written Opinion for Application No. PCT/US2010/033112, dated Nov. 1, 2011.
Crosson, Craig E., "Adenosine Receptor Activation Modulates Intraocular Pressure in Rabbits," The Journal of Pharmacology and Experimental Therapeutics, vol. 273(1):320-326 (1995).
Crosson, Craig E., "Ocular hypotensive activity of the adenosine agonist (R)-phenylisopropyladenosine in rabbits," Current Eye Research, vol. 11(5):453-458 (1992).
Tian, Baohe et al., "Effects of Adenosine Agonists on Intraocular Pressure and Aqueous Humor Dynamics in Cynomolgus Monkeys," Exp. Eye Res., vol. 64:979-989 (1997).
International Search Report and Written Opinion for Application No. PCT/US2010/033112, dated Jul. 21, 2010.
Appel, S. et al., "Modelling of the pharmacodynamic interaction of an A1 adenosine receptor agonist and antagonist in vivo: N6-cyclopentyladenosine and 8-cyclopentyltheophylline," British Journal of Pharmacology, vol. 115:1253-1259 (1995).
Avila, Marcel Y. et al., "A1-,A2A-and A3-subtype adenosine receptors modulate intraocular pressure in the mouse," British Journal of Pharmacology, vol. 134:241-245 (2001).
Bell, Jerald, A. et al., "Ocular Hypertension," eMedicine Ophthalmology, retreived online at: http://emedicine.medscape.com/article/1207470-overview (2008).
Crosson, Craig E. et al., "Characterization of Ocular Hypertension Induced by Adenosine Agonists," Investigative Ophthalmology & visual Science, vol. 37(9):1833-1839 (1996).
Crosson, Craig E. et al., "Intraocular Pressure Responses to the Adenosine Agonist Cyclohexyladenosine: Evidence for a Dual Mechanism of Action," Investigative Ophthalmology & Visual Science, vol. 42(8):1837-1840 (2001).
Crosson, Craig E. et al., "Modulation of Conventional Outflow Facility by the Adenosine A1 Agonist N6-Cyclohexyladenosine," Investigative Ophthalmology & Visual Science, vol. 46(10):3795-3799 (2005).
Crosson, Craig E. et al., "Modulation of Intraocular Pressure by Adenosine Agonists," Journal of Ocular Pharmacology, vol. 10(1):379-383 (1994).
Crosson, Craig E. et al., "Ocular effects associated with the chronic administration of the adenosine A1 agonist cyclohexyladenosine," Current Eye Research, vol. 21(4):808-813 (2000).
Daines, Bradley S. et al., "Intraocular Adenosine Levels in Normal and Ocular-Hypertensive Patients," Journal of Ocular Pharmacology and Therapeutics, vol. 19(2):113-119 (2003).
Fredholm, Bertil B. et al., "International Union of Pharmacology. XXV. Nomenclature and Classification of Adenosine Receptors," Pharmacological Reviews, vol. 53(4):527-552 (2001).
Hirao, Mami et al., "Effects of adenosine on optic nerve head circulation in rabbits," Experimental Eye Research, vol. 79:729-735 (2004).
Jacobson, Kenneth A. et al., "Adenosine receptors as therapeutic targets," Nature Reviews Drug Discovery, vol. 5:247-264 (2006).
Polska, Elzbieta et al., "Effects of Adenosine on Intraocular Pressure, Optic Nerve Head Blood Flow, and Choroidal Blood Flow in Healthy Humans," Investigative Ophthalmology & Visual Science, vol. 44(7):3110-3114 (2003).
Chinese Office Action for Application No. 201080018539.X, 9 pages, dated Nov. 2, 2012.

* cited by examiner

*Primary Examiner* — Lawrence E Crane
(74) *Attorney, Agent, or Firm* — Nelson Mullins Riley & Scarborough LLP; Jane E. Remillard, Esq.; Cynthia L. Kanik

(57) ABSTRACT

Provided herein are compounds, compositions, and methods for reducing intraocular pressure. Also provided herein are compounds, compositions and methods for the treatment of glaucoma or ocular hypertension.

42 Claims, 11 Drawing Sheets

Figure 4a. Responder Analysis

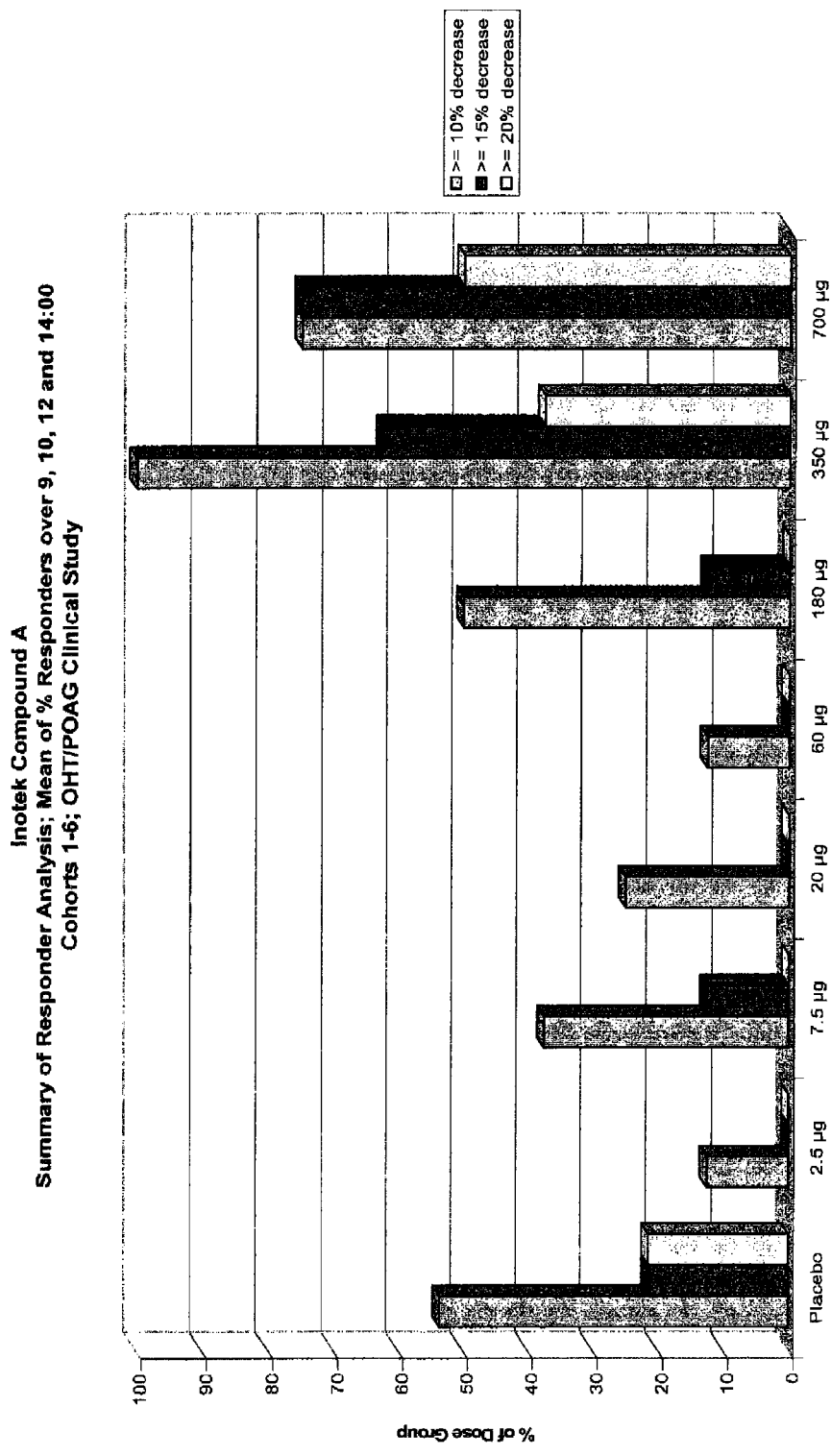
Figure 4b. Responder Analysis Using the Mean Responder Rate Over the Postdose Observation Period Figure 5  Summary of Responder Analysis; Mean of % Responders over 9, 10, 12, 14:00
Cohort 6; OHT/POAG Clinical Study Compound A

| Time points used to compute mean % change from BL | Mean % decrease from BL | | Median % decrease from BL | | % (n) subjects who have reduction of IOP ≥ 10% | | % (n) subjects who have reduction of IOP ≥ 15% | | % (n) subjects who have reduction of IOP ≥ 20% | |
|---|---|---|---|---|---|---|---|---|---|---|
| | Placebo (N=24) | 350 mcg (N=8) | Placebo (N=24) | 350 mcg (N=8) | Placebo (N=24) | 350 mcg (N=8) | Placebo (N=24) | 350 mcg (N=8) | Placebo (N=24) | 350 mcg (N=8) |
| 9AM, 10AM, 12AM, 2PM | -10.6 | -18.5 | -9 | -17.2 | 41.7% (10) | 100% (8) | 29.2% (7) | 62.5% (5) | 20.8% (5) | 37.5% (3) |
| 9AM, 10AM, 12AM | -9.5 | -16 | -7.9 | -14.9 | 37.5% (9) | 87.5% (5) | 20.8% (5) | 50.4% (4) | 12.5% (3) | 37.5% (3) |
| 9AM, 10AM | -8.3 | -13.5 | -5.5 | -13 | 33.3% (8) | 75% (6) | 16.7% (4) | 25% (2) | 8.3% (2) | 12.5% (1) |
| 10AM | -10 | -16.6 | -8.8 | -17.6 | 45.8% (11) | 87.5% (7) | 25% (6) | 75% (6) | 12.5% (3) | 37.5% (3) |
| 9AM | -6.6 | -10.3 | -4 | -9.4 | 33.3% (8) | 50% (4) | 20.8% (5) | 25% (2) | 8.3% (2) | 12.5% (1) |

Mean and Median % Change From Predose IOP of 350 mcg Cohort and Placebo
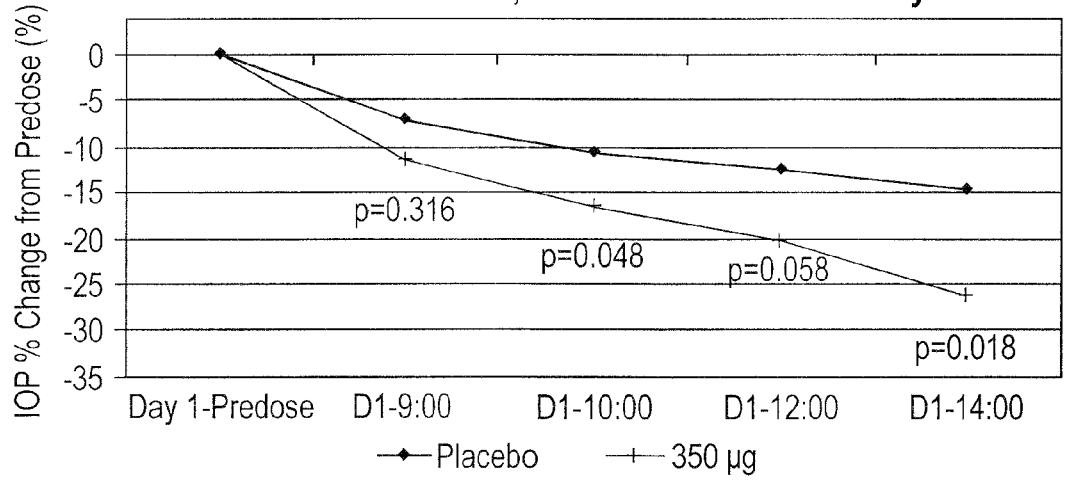
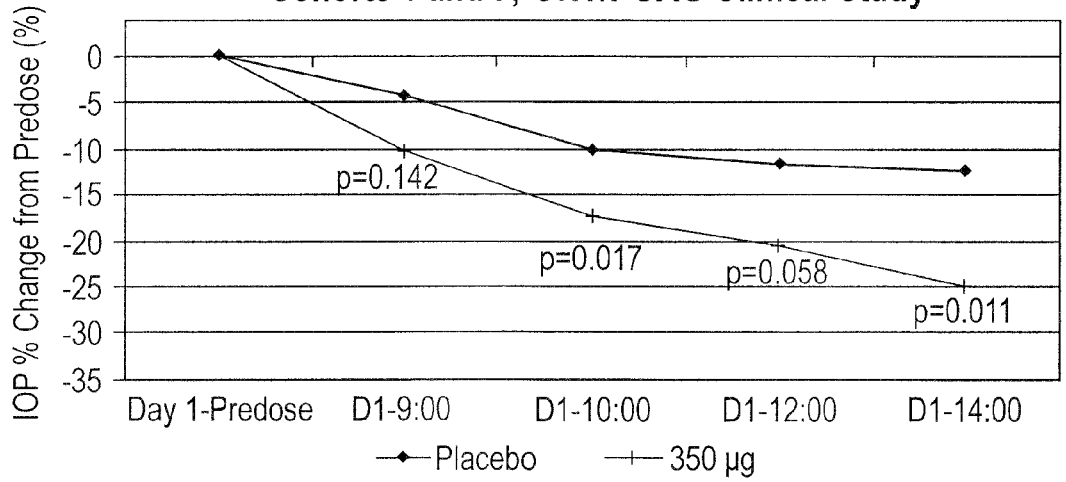
Figure 6

Figure 7

Compound A
Summary of Responder Analysis; Mean of % Responders over 9, 10, 14 and 18:00
700 mcg Cohort 7; OHT/POAG Clinical Study

| Time points used to compute mean % change from BL | Mean % decrease from BL | | Median % decrease from BL | | % (n) subjects who have reduction of IOP ≥ 10% | | % (n) subjects who have reduction of IOP ≥ 15% | | % (n) subjects who have reduction of IOP ≥ 20% | |
|---|---|---|---|---|---|---|---|---|---|---|
| | Placebo (N=28) | 700 mcg (N=8) | Placebo (N=28) | 700 mcg (N=8) | Placebo (N=28) | 700 mcg (N=8) | Placebo (N=28) | 700 mcg (N=8) | Placebo (N=28) | 700 mcg (N=8) |
| 9AM, 10AM, 14PM, 18PM | -11.1 | -17.4 | -10.8 | -18.4 | 53.6% (15) | 75% (6) | 25% (7) | 75% (6) | 21.4% (6) | 37.5% (3) |
| 9AM, 10AM, 14PM | -10.8 | -16.6 | -10.5 | -19.5 | 53.6% (15) | 75% (6) | 21.4% (6) | 75% (6) | 21.4% (6) | 50% (4) |
| 9AM, 10AM | -8.9 | -14.8 | -6.7 | -16 | 39.3% (11) | 75% (6) | 21.4% (6) | 62.5% (5) | 7.1% (2) | 25% (2) |
| 10AM | -10.7 | -17.3 | -10.2 | -20.4 | 50% (14) | 87.5% (7) | 32.1% (8) | 62.5% (5) | 14.3% (4) | 50% (4) |
| 9AM | -7.1 | -12.4 | -4.1 | -9.6 | 39.3% (11) | 50% (4) | 21.4% (6) | 25% (2) | 7.1% (2) | 12.5% (1) |

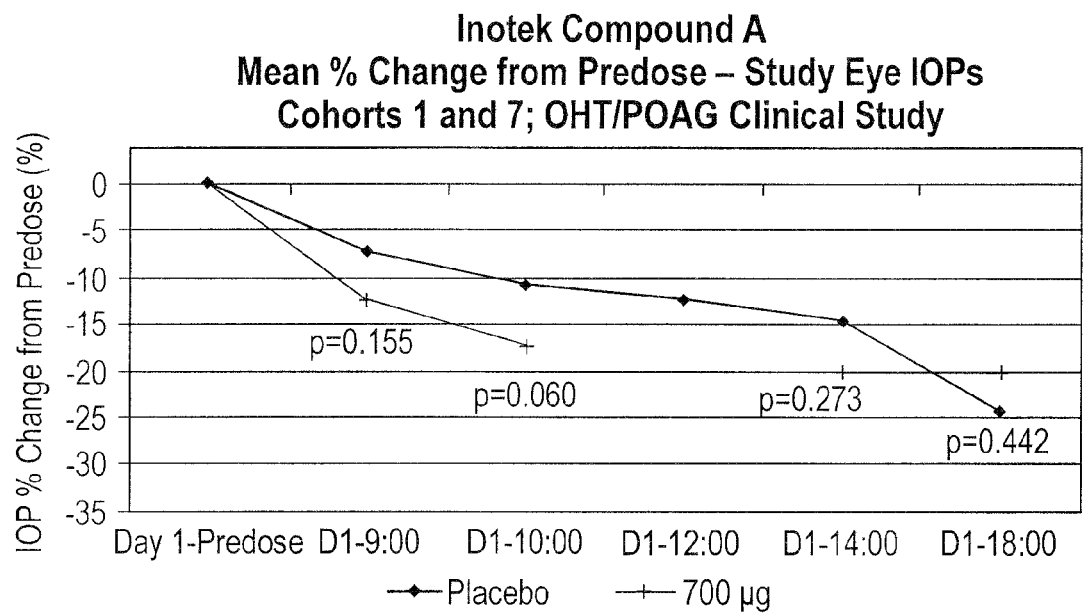
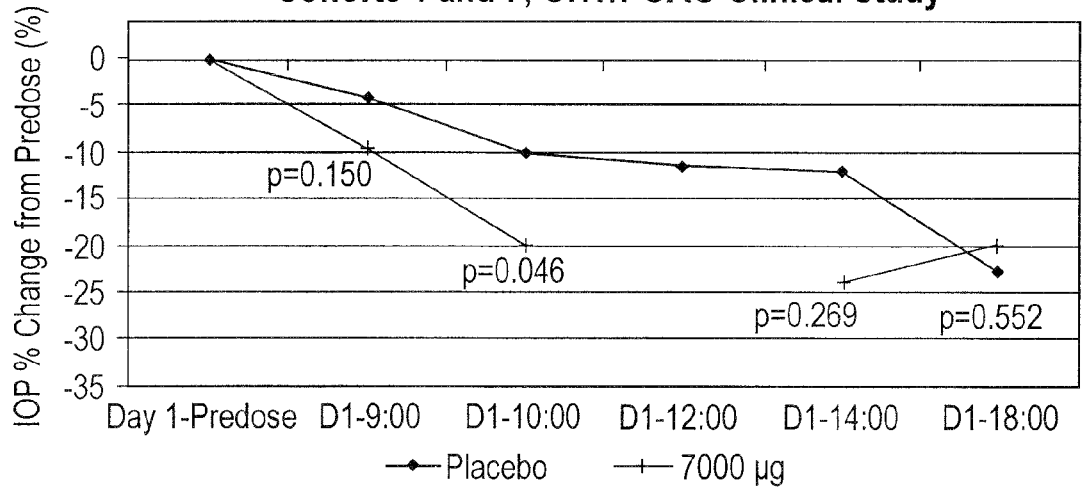
Figure 8

METHOD OF REDUCING INTRAOCULAR PRESSURE IN HUMANS

CROSS-REFERENCE TO RELATED APPLICATIONS

This application claims priority to U.S. Provisional Application No. 61/174,655, filed May 1, 2009. This application also claims priority to U.S. Provisional Application No. 61/219,990, filed Jun. 24, 2009. The entire contents of the aforementioned applications and any patents, patent applications, and references cited throughout this specification are herein hereby incorporated by reference in their entireties.

TECHNICAL FIELD OF THE INVENTION

Provided herein are methods of reducing intraocular pressure (IOP) in humans. Also provided herein are uses of certain compounds in human subjects for reducing and/or controlling elevated or abnormally fluctuating IOPs in the treatment of glaucoma or ocular hypertension (OHT).

BACKGROUND OF THE INVENTION

Glaucoma refers to a group of optic neuropathies that are characterized by loss of retinal ganglion cells and atrophy of the optic nerve with resultant visual field loss. The disease is the leading cause of irreversible blindness worldwide and the second leading cause of blindness, behind cataracts. Clinical trials have demonstrated that elevated IOP is a major risk factor for glaucoma and have validated the role of lowering IOP in the management of glaucoma.

Glaucoma is classified according to three parameters: 1) the underlying cause, i.e., primary (idiopathic) or secondary (associated with some other ocular or systemic conditions); 2) the state of the anterior chamber angle, i.e., open angle (open access of the outflowing aqueous humor to trabecular meshwork) or closed angle (narrow angle; the trabecular meshwork is blocked by apposition of the peripheral iris and the cornea); and 3) chronicity, i.e., acute or chronic. Although secondary forms of glaucoma with clear etiologies do exist (e.g., pseudoexfoliation and pigmentary dispersion), the most common form of glaucoma is primary open angle glaucoma (POAG).

OHT is a condition in which IOP is elevated but no glaucomatous findings have been observed (Bell, 2005). The Ocular Hypertension Study demonstrated that patients with OHT have an overall risk of 10% over 5 years of developing glaucoma and that this risk can be cut in half by the institution of medical treatment that reduces IOP.

Drug therapies that have proven to be effective for the reduction of intraocular pressure include both agents that decrease aqueous humor production and agents that increase the outflow facility. Such therapies are in general administered by one of two possible routes: topically (direct application to the eye) or orally. However, pharmaceutical ocular anti-hypertension approaches have exhibited various undesirable side effects. For example, miotics such as pilocarpine can cause blurring of vision, headaches, and other negative visual side effects. Systemically administered carbonic anhydrase inhibitors can also cause nausea, dyspepsia, fatigue, and metabolic acidosis. Certain prostaglandins cause hyperemia, ocular itching, and darkening of eyelashes and periorbital tissues. Further, certain beta-blockers have increasingly become associated with serious pulmonary side-effects attributable to their effects on beta-2 receptors in pulmonary tissue. Sympathomimetics cause tachycardia, arrhythmia and hypertension. Such negative side-effects may lead to decreased patient compliance or to termination of therapy such that normal vision continues to deteriorate. Additionally, there are individuals who simply do not respond well when treated with certain existing glaucoma therapies.

There is, therefore, a need for other therapeutic agents that control IOP.

SUMMARY OF THE INVENTION

Provided herein are compounds, pharmaceutical compositions comprising such compounds, and methods of using such compounds to treat or prevent diseases or disorders associated with elevated intraocular pressure. In one embodiment the diseases and conditions caused by elevated IOP in a human are selected from the group consisting of normal-tension glaucoma, OHT, and POAG.

Thus, in a first aspect there is provided a method of reducing intraocular pressure comprising the step of: applying an effective amount of an ophthalmic pharmaceutical composition to an affected eye of a human, the composition comprising an effective amount of a compound according to Formula I,

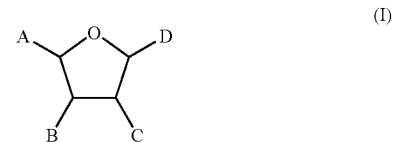

or a pharmaceutically acceptable salt thereof,
wherein
A is —CH$_2$ONO$_2$—CH$_2$OSO$_3$H;
B and C are —OH; and
D is

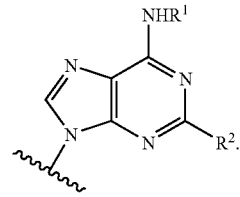

In one embodiment the method comprises applying from about 0.05 mg/ml to about 7.0 mg/ml of a compound according to Formula I from 1 to 4 times daily. In another embodiment the method comprises applying from about 20-700 µg of a compound according to Formula I from 1 to 2 times daily. In another embodiment the method comprises applying about 350 µg of a compound according to Formula I from 1 to 2 times daily.

When practicing the method, the compound can be administered in drops, e.g., 1 to 2 drops. In one embodiment the IOP of the affected eye is reduced by at least 10%, e.g., at least 10-20%, e.g., by 20% or more. In one embodiment the IOP of the affected eye is reduced by at least 10% for more than 3 hours, e.g., at least 10-20% for more than 3 hours, e.g., by 20% or more for more than 3 hours. In one embodiment the IOP of the affected eye is reduced by at least 10% for at least 6 hours.

In another embodiment the method further includes prior, simultaneous or sequential, application of a second IOP-reducing agent. The second IOP-reducing agent is selected from the group consisting of β-blockers, prostaglandin analogs, carbonic anhydrase inhibitors, rho-kinase inhibitors, $\alpha_2$ agonists, miotics, neuroprotectants, A3 antagonists, A2A agonists, ion channel modulators and combinations thereof.

In a second aspect the present invention is directed to a method of reducing IOP and associated diseases and conditions caused by elevated IOP in a human subject by administering an effective amount of a selective A1 agonist to an affected eye of the subject. In one embodiment the diseases and conditions caused by elevated IOP in a human are selected from the group consisting of normal-tension glaucoma, OHT, and POAG. The selective A1 agonist can be a compound of Formula I as defined above.

When practicing the method, the selective A1 agonist can be administered in drops, e.g., 1 to 2 drops. In one embodiment of this method, the IOP of the affected eye is reduced by at least 10%, e.g., at least 10-20%, e.g., by 20% or more. In one embodiment the IOP of the affected eye is reduced by at least 10% for more than 3 hours, e.g., at least 10-20% for more than 3 hours, e.g., by 20% or more for more than 3 hours. In one embodiment the IOP of the affected eye is reduced by at least 10% for at least 6 hours.

In one embodiment of the methods described herein, the effective amount of the selective adenosine A1 agonist is at least 20 μg, e.g., between 60 μg and 350 μg, e.g., between 60 μg and 700 μg.

In one embodiment the effective amount of the selective adenosine A1 agonist is administered as a single dose. In another embodiment, the effective amount of the selective adenosine A1 agonist is administered as a twice daily dose.

In another aspect there is provided an ophthalmic pharmaceutical composition comprising a compound of Formula I as defined above and a pharmaceutically acceptable vehicle or excipient. The pharmaceutically acceptable vehicle or excipient can be selected from the group consisting of: opthalmologically acceptable preservatives, surfactants, viscosity enhancers, penetration enhancers, gelling agents, hydrophobic bases, vehicles, buffers, sodium chloride, and water.

In one embodiment the composition further comprises a second IOP reducing agent in addition to a compound of Formula I as defined above. The second IOP reducing agent can be selected from the group comprising: β-blockers, prostaglandin analogs, carbonic anhydrase inhibitors, rho-kinase inhibitors, $\alpha_2$ agonists, miotics, neuroprotectants, A3 antagonists, A2A agonists, ion channel modulators and combinations thereof.

The therapeutic composition can comprise from about 0.05 mg/ml to about 7.0 mg/ml, e.g., about 0.4 mg/ml to about 7.0 mg/ml, of said compound of Formula I.

In one embodiment the compound of Formula I is selected from the group consisting of: ((2R,3S,4R,5R)-5-(6-(cyclopentylamino)-9H-purin-9-yl)-3,4-dihydroxytetrahydrofuran-2-yl)methyl nitrate; ((2R,3S,4R,5R)-5-(2-chloro-6-(cyclopentylamino)-9H-purin-9-yl)-3,4-dihydroxytetrahydrofuran-2-yl)methyl nitrate; sodium ((2R,3S,4R,5R)-5-(6-(cyclopentylamino)-9H-purin-9-yl)-3,4-dihydroxytetrahydrofuran-2-yl)methyl sulfate; ((2R,3S,4R,5R)-3,4-dihydroxy-5-(6-(tetrahydrofuran-3-ylamino)-9H-purin-9-yl)tetrahydrofuran-2-yl)methyl nitrate; ((2R,3S,4R,5R)-5-(6-(cyclohexylamino)-9H-purin-9-yl)-3,4-dihydroxytetrahydrofuran-2-yl)methyl nitrate; ((2R,3S,4R,5R)-5-(6-(bicycle-[2.2.1]-heptan-2-ylamino)-9H-purin-9-yl)-3,4-dihydroxytetrahydrofuran-2-yl)methyl nitrate; sodium ((2R,3S,4R,5R)-5-(2-chloro-6-(cyclohexylamino)-9H-purin-9-yl)-3,4-dihydroxytetrahydrofuran-2-yl)methyl sulfate; and ((2R,3S,4R,5R)-5-(2-chloro-6-(cyclohexylamino)-9H-purin-9-yl)-3,4-dihydroxytetrahydrofuran-2-yl)methyl nitrate.

In a further aspect the selective adenosine A1 agonist compounds of Formula I can be used to lower and/or control IOP associated with normal-tension glaucoma, OHT, and POAG in humans. In certain embodiments, when used to treat normal-tension glaucoma or OHT, the compounds of Formula I can be formulated in pharmaceutically acceptable compositions suitable for topical delivery to the eye.

Another embodiment of the present invention comprises an ophthalmic pharmaceutical composition useful in the reduction of intraocular pressure, comprising an effective amount of a compound according to Formula I.

In another aspect of the invention, there is provided an ophthalmic formulation for reducing intraocular pressure, comprising about 0.05 mg·ml to about 7 mg/ml of a compound of Formula I as defined above and from 1 mg/ml to about 140 mg/ml of hydroxypropyl β-cyclodextrin in saline for injection.

In one embodiment the formulation comprises about 7 mg/ml of a compound of Formula I selected from: ((2R,3S,4R,5R)-5-(2-chloro-6-(cyclopentylamino)-9H-purin-9-yl)-3,4-dihydroxytetrahydrofuran-2-yl)methyl nitrate; sodium ((2R,3S,4R,5R)-5-(6-(cyclopentylamino)-9H-purin-9-yl)-3,4-dihydroxytetrahydrofuran-2-yl)methyl sulfate; and ((2R,3S,4R,5R)-3,4-dihydroxy-5-(6-(tetrahydrofuran-3-ylamino)-9H-purin-9-yl)tetrahydrofuran-2-yl)methyl nitrate.

It is to be further appreciated that the use of compounds of Formula I as defined above, or ophthalmic compositions as defined above may be used for manufacture of a medicament for reducing IOP in an affected eye of a human subject.

The foregoing brief summary broadly describes the features and technical advantages of certain embodiments of the present invention. Further technical advantages will be described in the detailed description of the invention that follows. Novel features which are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to be definitions of the invention's scope.

BRIEF DESCRIPTION OF THE DRAWINGS

FIG. 4a presents a summary chart of the responder analysis in the 7 treatment groups at approximately 2 hours post-dose where the largest portion of the difference in IOP between drug-treated and placebo-treated eyes is apparent.

FIG. 4b presents a summary chart of the responder analysis in the 7 treatment groups using the mean responder rate over a 6 hour postdose observation period.

FIG. 5 shows the mean and median % decrease from baseline (BL; predose) and the categorical responder analysis of the 350 mcg cohort over the entire postdose observation period FIG. 6 shows the statistically significant percent decrease in the mean and median IOPs (from the predose baseline IOP determinations) observed in the 350 mcg cohort relative to the placebo response.

FIG. 7 shows the mean and median % decrease from baseline (BL; predose) and the categorical responder analysis of the 700 mcg cohort over a 10 hour postdose observation period.

FIG. 8 shows the statistically significant percent decrease in the mean and median IOPs (from the predose baseline IOP determinations) observed in the 700 mcg cohort relative to the placebo response.

DETAILED DESCRIPTION OF THE INVENTION

Figure 1:
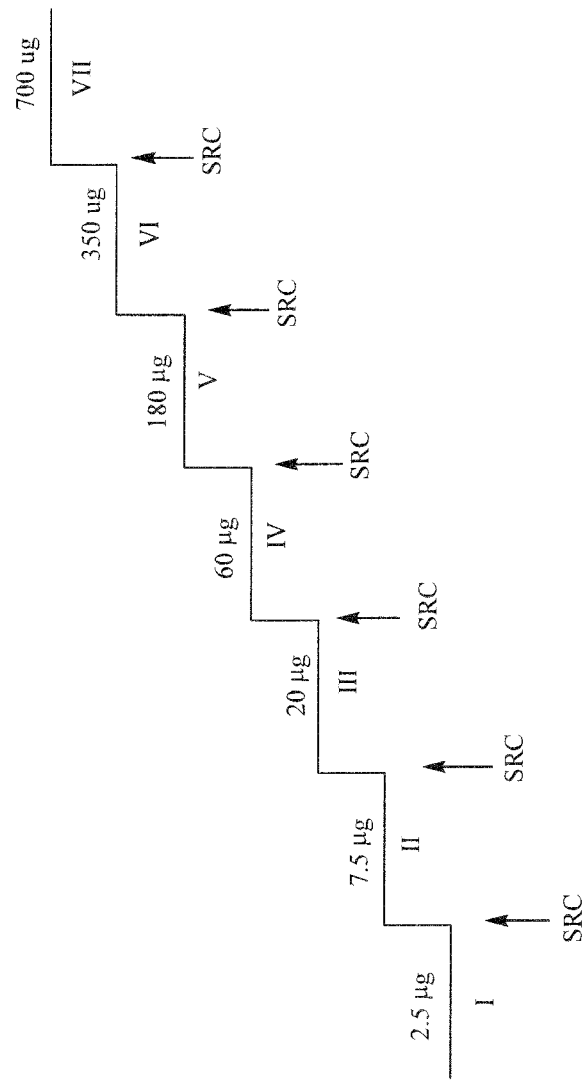
FIG. 1 shows the dose escalation scheme over the 7 treatment groups of the multi-center, randomized, double-blinded clinical study. Twelve subjects were randomly assigned to each treatment group: 8 subjects received Compound A and 4 subjects received placebo.

Embodiments of the present invention provide compounds useful for treating reducing and controlling normal or elevated intraocular pressure (IOP) and/or treating glaucoma.

Adenosine is a purine nucleoside that modulates many physiologic processes. Cellular signaling by adenosine occurs through four adenosine receptor subtypes: $A_1$, $A_{2A}$, $A_{2B}$, and $A_3$ as reported by Ralevic and Burnstock (Pharmacol Rev. 50:413-492, 1988) and Fredholm B B et al. (Pharmacol Rev. 53:527-552, 2001). In the eye, adenosine $A_1$ receptor agonists lower IOP in mice, rabbits and monkeys (Tian B et al. Exp Eye Res. 64:979-989, 1997; Crosson C E. J Pharmacol Exp Ther. 273: 320-326, 1995; and Avila M Y et al. Br J. Pharmacol. 134:241-245, 2001). While other publications have noted that adenosine A1 receptor agonists in the eye target the conventional outflow pathway via the trabecular meshwork (Husain S et al. J Pharmacol Exp Ther. 320: 258-265, 2007), reduction of IOP via other pathways has not been excluded.

It should be noted that the highly robust, adenosine $A_1$ receptor-mediated drop in IOP reported in preclinical studies is often preceded by an immediate, yet transient elevation in IOP following instillation of the A1 receptor ligand (Crosson C E and Grey T. Inv Ophthal Visual Sci. 37, [9] 1833-1839, 1996). Transient elevations in IOP of ~3-9 mmHg have been observed in a ~30 min "window" after dosing. This phenomenon may arise from cross-reactivity between adenosine receptor sub-types within the eye. Pharmacological studies indicate that this transient elevation in IOP might be due, at least in part, to the activation of adenosine $A_{2B}$ receptors (Crosson, 1996). Therefore, development of a highly-selective A1 agonist that only reduce IOP would appear to be more tenable than the development of adenosine A2-receptor-based drugs for treating IOP, as A2A agonists may increase, decrease or exert mixed effects on IOP (Konno, 2004; Konno, J Pharmacol Sci., 2005; Konno, Eur J. Pharmacol. 2005).

Compounds that act as selective adenosine A1 agonists are known and have shown a variety of utilities. U.S. Pat. No. 7,423,144 to Jagtap et al. describes such selective adenosine A1 agonists compounds for the prevention or treatment of tachyarrhythmias (elevated heart rate), pain disorders, and ischemia-reperfusion injury.

Selective adenosine A1 agonists have been discovered to reduce IOP in humans in clinical studies. In particular, described herein are compounds of Formula I (e.g., Compounds A, B, C, D, E, F, G or H) that can reduce intraocular pressure in a subject (e.g., a human) in need thereof.

Compounds of Formula I have the following structure:

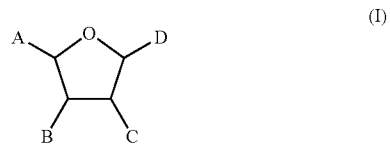
(I)

or a pharmaceutically acceptable salt thereof, wherein
A is —$CH_2ONO_2$ or —$CH_2OSO_3H$;
B and C are —OH;
D is

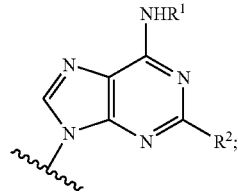

A and B are trans with respect to each other;
B and C are cis with respect to each other;
C and D are cis or trans with respect to each other;
$R^1$ is —H, —$C_1$-$C_{10}$ alkyl, -aryl, -3- to 7-membered monocyclic heterocycle, -8- to 12-membered bicyclic heterocycle, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;
$R^2$ is —H, halo, —CN, —$NHR^4$, —$NHC(O)R^4$, —$NHC(O)OR^4$, —$NHC(O)NHR^4$, —$NHNHC(O)R^4$, —$NHNHC(O)OR^4$, —$NHNHC(O)NHR^4$, or —NH—N=C($R^6$)$R^7$;
$R^4$ is —$C_1$-$C_{15}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —C≡C—($C_1$-$C_{10}$alkyl) or —C≡C-aryl;
$R^6$ is —$C_1$-$C_{10}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$—($C_3$-$C_8$ monocyclic cycloalkenyl), -phenylene-$(CH_2)_n$COOH, or -phenylene-$(CH_2)_n$COO—($C_1$-$C_{10}$ alkyl);
$R^7$ is —H, —$C_1$-$C_{10}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkenyl) or —$(CH_2)_n$—($C_8$-$C_{12}$ bicyclic cycloalkyl); and
each n is independently an integer ranging from 1 to 5, and a pharmaceutically acceptable vehicle.

In a further embodiment, the compounds for use in the invention are compounds having the formula

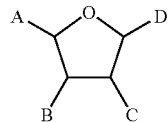 (Ia)

or a pharmaceutically acceptable salt thereof, wherein

A is —CH$_2$ONO$_2$ or —CH$_2$OSO$_3$H;
B and C are —OH;
D is

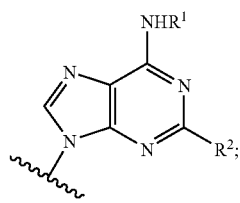

A and B are trans with respect to each other;
B and C are cis with respect to each other;
C and D are cis or trans with respect to each other;
R$^1$ is —C$_3$-C$_8$ monocyclic cycloalkyl, -3- to 7-membered monocyclic heterocycle, or —C$_8$-C$_{12}$ bicyclic cycloalkyl; and
R$^2$ is —H or -halo.

In a further embodiment, the compounds for use in the invention are compounds having the formula

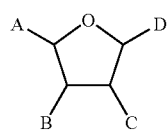 (Ib)

or a pharmaceutically acceptable salt thereof, wherein

A is —CH$_2$ONO$_2$;
B and C are —OH;
D is

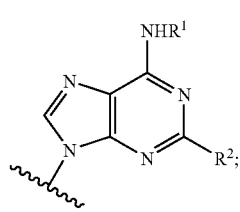

A and B are trans with respect to each other;
B and C are cis with respect to each other;
C and D are cis or trans with respect to each other;
R$^1$ is —C$_3$-C$_8$ monocyclic cycloalkyl, -3- to 7-membered monocyclic heterocycle, or —C$_8$-C$_{12}$ bicyclic cycloalkyl; and
R$^2$ is —H or -halo.

In another embodiment, the compound of Formula I is one of the following compounds:

Compound A

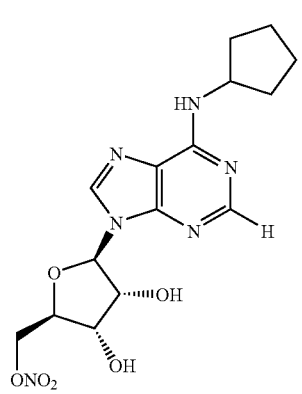

((2R,3S,4R,5R)-5-(6-(cyclopentylamino)-9H-purin-9-yl)-3,4-dihydroxytetrahydrofuran-2-yl)methyl nitrate, Compound B

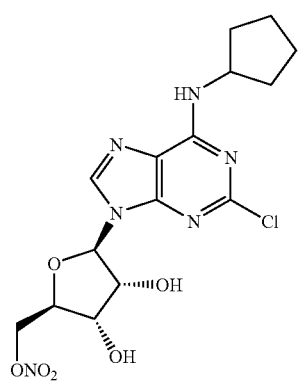

((2R,3S,4R,5R)-5-(2-chloro-6-(cyclopentylamino)-9H-purin-9-yl)-3,4-dihydroxytetrahydrofuran-2-yl)methyl nitrate, Compound C

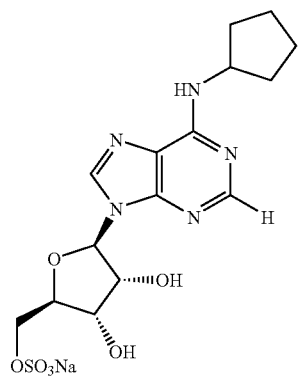

sodium ((2R,3S,4R,5R)-5-(6-(cyclopentylamino)-9H-purin-9-yl)-3,4-dihydroxytetrahydrofuran-2-yl)methyl sulfate,

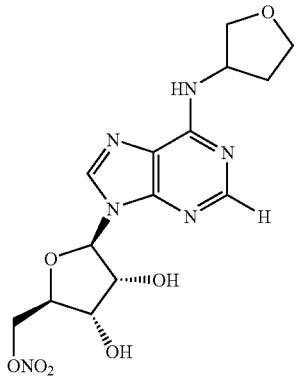

Compound D ((2R,3S,4R,5R)-3,4-dihydroxy-5-(6-(tetrahydrofuran-3-ylamino)-9H-purin-9-yl)tetrahydrofuran-2-yl)methyl nitrate,

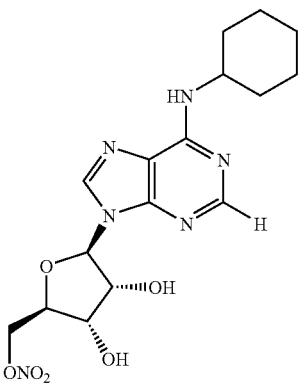

Compound E ((2R,3S,4R,5R)-5-(6-(cyclohexylamino)-9H-purin-9-yl)-3,4-dihydroxytetrahydrofuran-2-yl)methyl nitrate,

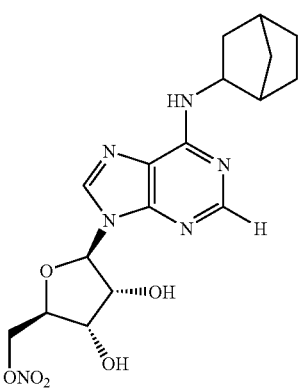

Compound F ((2R,3S,4R,5R)-5-(6-(bicycle-[2.2.1]-heptan-2-ylamino)-9H-purin-9-yl)-3,4-dihydroxytetrahydrofuran-2-yl)methyl nitrate,

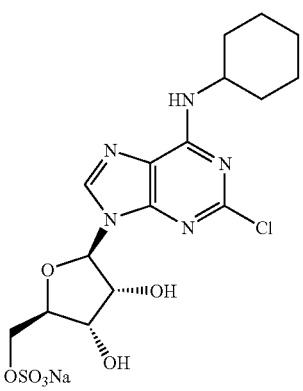

Compound G sodium ((2R,3S,4R,5R)-5-(2-chloro-6-(cyclohexylamino)-9H-purin-9-yl)-3,4-dihydroxytetrahydrofuran-2-yl)methyl sulfate, and

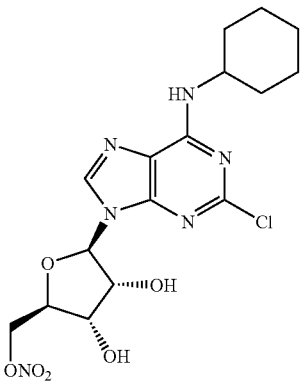

Compound H ((2R,3S,4R,5R)-5-(2-chloro-6-(cyclohexylamino)-9H-purin-9-yl)-3,4-dihydroxytetrahydrofuran-2-yl)methyl nitrate, or pharmaceutically acceptable salts thereof.

Where discrepancies exist between a compound's name and a compound's structure, the chemical structure will control.

In one embodiment, provided herein is a method of reducing intraocular pressure, comprising administering an effective amount of a compound of Formula I to a human. In another embodiment, provided herein is a method of reducing intraocular pressure, comprising applying an effective amount of a compound of Formula I to an affected eye of a human. In yet another embodiment, provided herein is a method of treating glaucoma, comprising administering to an affected eye of a human an effective amount of a compound of Formula I. In another embodiment, provided herein is a method of treating OHT, comprising administering to an affected eye of a human an effective amount of a compound of Formula I. In another embodiment, provided herein is a method of treating POAG, comprising administering to an affected eye of a human an effective amount of a compound of Formula I. In another embodiment, about 0.05 mg/ml to about 7.0 mg/ml of a compound of Formula I is applied to an affected eye of a human from 1 to 4 times daily. In one embodiment, about 20-700 µg of a compound of Formula I is applied to an affected eye of a human from 1 to 4 times daily. In still another embodiment, about 350 µg of a compound of Formula I is applied to an affected eye of a human from 1 to 4 times daily. A compound of Formula I can be administered in drops, e.g., 1 to 2 drops.

In another embodiment, provided herein is a method of reducing intraocular pressure, comprising administering an effective amount of Compound A to a human. In still another embodiment, provided herein is a method of reducing intraocular pressure, comprising applying an effective amount of Compound A to an affected eye of a human. In yet another embodiment, provided herein is a method of treating glaucoma, comprising administering to an affected eye of a human an effective amount of Compound A. In another embodiment, provided herein is a method of treating OHT, comprising administering to an affected eye of a human an effective amount of Compound A. In still another embodiment, provided herein is a method of treating POAG, comprising administering to an affected eye of a human an effective amount of Compound A. In one embodiment, about 0.05 mg/ml to about 7.0 mg/ml to of Compound A is applied to an affected eye of a human from 1 to 4 times daily. In one embodiment, about 20-700 µg of Compound A is applied to an affected eye of a human from 1 to 4 times daily. In another embodiment, about 350 µg of Compound A is applied to an affected eye of a human from 1 to 4 times daily. The Compound A can be administered in drops, e.g., 1 to 2 drops.

In another embodiment, provided herein is a topical ophthalmic formulation for reducing intraocular pressure in a human comprising 0.05 mg·ml to about 7 mg/ml of Compound A, and from 1 mg/ml to about 140 mg/ml of hydroxypropyl β-cyclodextrin in saline for injection. This formulation can be used to treat n glaucoma, OHT, or POAG in a human.

In another embodiment, provided herein is the use of a compound of Formula I for the manufacture of a medicament for reducing intraocular pressure in a subject. In another embodiment, provided herein is the use of a compound of Formula I for the manufacture of a medicament for treating glaucoma in a subject. In another embodiment, provided herein is the use of a compound of Formula I for the manufacture of a medicament for treating OHT in a subject. In another embodiment, provided herein is the use of a compound of Formula I for the manufacture of a medicament for treating POAG in a subject.

In another embodiment, provided herein is the use of a compound of Formula I for reducing intraocular pressure in a subject. In another embodiment, provided herein is the use of a compound of Formula I for treating glaucoma in a subject. In another embodiment, provided herein is the use of a compound of Formula I for treating OHT in a subject. In another embodiment, provided herein is the use of a compound of Formula I for treating POAG in a subject.

In another embodiment, provided herein is the use of Compound A for reducing intraocular pressure in a subject. In another embodiment, provided herein is the use of Compound A for treating glaucoma in a subject. In another embodiment, provided herein is the use of Compound A for treating OHT in a subject. In another embodiment, provided herein is the use of Compound A for treating POAG in a subject.

It is recognized that compounds of Formula 1 can contain one or more chiral centers. This invention contemplates all enantiomers, diastereomers, and mixtures of Formulas I thereof.

Furthermore, certain embodiments of the present invention comprise pharmaceutically acceptable salts of compounds according to Formula I.

Pharmaceutically acceptable salts comprise, but are not limited to, soluble or dispersible forms of compounds according to Formula I that are suitable for treatment of disease without undue undesirable effects such as allergic reactions or toxicity.

Representative pharmaceutically acceptable salts include, but are not limited to, acid addition salts such as acetate, citrate, benzoate, lactate, or phosphate and basic addition salts such as lithium, sodium, potassium, or aluminum.

DEFINITIONS

As used herein, the term "selective adenosine $A_1$ agonist" means an $A_1$ agonist that has a high affinity to the $A_1$ receptor while simultaneously having a low affinity for the $A_2$ and $A_3$ adenosine receptors. Compounds of Formula I (e.g., Compounds A to H) above have affinities to the $A_1$ receptor considerably greater than their respective affinities to the $A_{2A}$ and $A_3$ receptors. The $A_1$ selectivity data for compounds A to H is summarized in the Table below.

| Compound | $A_1$ (Ki (nm)) POTENCY | $A_1 > A_{2A}$ SELECTIVITY [KiA$_2$(nm)/ KiA$_1$(nm)] | $A_1 > A_3$ SELECTIVITY [KiA$_3$(nm)/ KiA$_1$(nm)] |
|---|---|---|---|
| CPA | 2.3 | 345 | 31.3 |
| CCPA | 0.83 | 2735 | 50 |
| Compound A | 0.97 | 4837 | 725 |
| Compound B | 2.63 | 1593 | 195 |
| Compound C | 4.05 | 2250 | 251 |
| Compound D | 10.6 | >9434 | 202 |
| Compound E | 1.32 | 878 | 1098 |
| Compound F | 1.47 | 3945 | 260 |
| Compound G | 1.36 | 200 | 130 |
| Compound H | 8 | 192 | 167 |

In another embodiment, for the purposes of the present invention, a selective $A_1$ agonist is considered a compound that has a selectivity of $A_1$ binding affinity relative to the $A_3$ binding affinity greater than about 130 (i.e., $A_1 > A_3$ [KiA$_3$ (nm)/KiA$_1$ (nm)]).

CPA and CCPA are examples of known A1 agonists. However, these compounds have a lower A1 receptor/A3 receptor selectivity ratio:

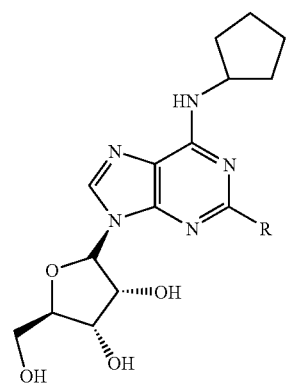

when R=H=cyclopentyladenosine (CPA) and when R=Cl=2-chloro cyclopentyladenosine (CCPA).

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-15 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl. The term alkyl includes, but is not limited to, $C_1$-$C_{15}$ alkyl, $C_1$-$C_{10}$ alkyl and $C_1$-$C_6$ alkyl.

The term "$C_1$-$C_{15}$ alkyl" as used herein refers to a straight or branched chain, saturated hydrocarbon having from 1 to 15 carbon atoms. Representative $C_1$-$C_{15}$ alkyl groups include, but are not limited to methyl, ethyl, propyl, isopropyl, butyl, sec-butyl, tert-buty, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl, neodecyl, undecyl, dodecyl, tridecyl, tetradecyl and pentadecyl. In one embodiment, the $C_1$-$C_{15}$ alkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_{15}$ alkyl is unsubstituted.

The term "$C_1$-$C_{10}$ alkyl" as used herein refers to a straight or branched chain, saturated hydrocarbon having from 1 to 10 carbon atoms. Representative $C_1$-$C_{10}$ alkyl groups include, but are not limited to methyl, ethyl, propyl, isopropyl, butyl, sec-butyl, tert-butyl, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl and neodecyl. In one embodiment, the $C_1$-$C_{10}$ alkyl group is substituted with one or more of the following groups: -halo, —O—($C_1$-$C_6$ alkyl), —OH, —CN, —COOR', —OC(O)R', —N(R)$_2$, —NHC(O)R' or —C(O)NHR' groups wherein each R' is independently —H or unsubstituted —$C_1$-$C_6$ alkyl. Unless indicated, the $C_1$-$C_{10}$ alkyl is unsubstituted. $C_1$-$C_{10}$ alkyl includes, but is not limited to, $C_1$-$C_6$ alkyl.

The term "$C_1$-$C_6$ alkyl" as used herein refers to a straight or branched chain; saturated hydrocarbon having from 1 to 6 carbon atoms. Representative $C_1$-$C_6$ alkyl groups include, but are not limited to methyl, ethyl, propyl, isopropyl, butyl, sec-butyl, tert-buty, pentyl, isopentyl, neopentyl, hexyl, isohexyl, and neohexyl. Unless indicated, the $C_1$-$C_6$ alkyl is unsubstituted.

The term "aryl" as used herein refers to a phenyl group or a naphthyl group. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the aryl is unsubstituted.

The term "$C_3$-$C_8$ monocyclic cycloalkyl" as used herein is a 3-, 4-, 5-, 6-, 7- or 8-membered saturated non-aromatic monocyclic cycloalkyl ring. Representative $C_3$-$C_8$ monocyclic cycloalkyl groups include, but are not limited to, cyclopropyl, cyclobutyl, cyclopentyl, cyclohexyl, cycloheptyl and cyclooctyl. In one embodiment, the $C_3$-$C_8$ monocyclic cycloalkyl group is substituted with one or more of the following groups: -halo, —O—($C_1$-$C_6$ alkyl), —OH, —CN, —COOR', —OC(O)R', —N(R)$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkyl is unsubstituted.

The term "$C_3$-$C_8$ monocyclic cycloalkenyl" as used herein is a 3-, 4-, 5-, 6-, 7- or 8-membered non-aromatic monocyclic carbocyclic ring having at least one endocyclic double bond, but which is not aromatic. It is to be understood that when any two groups, together with the carbon atom to which they are attached form a $C_3$-$C_8$ monocyclic cycloalkenyl group, the carbon atom to which the two groups are attached remains tetravalent. Representative $C_3$-$C_8$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl, 1,3,5-cycloheptatrienyl, cyclooctenyl, 1,3-cyclooctadienyl, 1,4-cyclooctadienyl, or 1,3,5-cyclooctatrienyl. In one embodiment, the $C_3$-$C_8$ monocyclic cycloalkenyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkenyl is unsubstituted.

The term "$C_8$-$C_{12}$ bicyclic cycloalkyl" as used herein is a 8-, 9-, 10-, 11- or 12-membered saturated, non-aromatic bicyclic cycloalkyl ring system. •Representative $C_8$-$C_{12}$ bicyclic cycloalkyl groups include, but are not limited to, decahydronaphthalene, octahydroindene, decahydrobenzocycloheptene, and dodecahydroheptalene. In one embodiment, the $C_8$-$C_{12}$ bicyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_8$-$C_{12}$ bicyclic cycloalkyl is unsubstituted.

The term "$C_8$-$C_{12}$ bicyclic cycloalkenyl" as used herein is a 8-, 9-, 10-, 11- or 12-membered non-aromatic bicyclic cycloalkyl ring system, having at least one endocyclic double bond. It is to be understood that when any two groups, together with the carbon atom to which they are attached form a $C_8$-$C_{12}$ bicyclic cycloalkenyl group, the carbon atom to which the two groups are attached remains tetravalent. Representative $C_8$-$C_{12}$ bicyclic cycloalkenyl groups include, but are not limited to, octahydronaphthalene, hexahydronaphthalene, hexahydroindene, tetrahydroindene, octahydrobenzocycloheptene, hexahydrobenzocycloheptene, tetrahydrobenzocycloheptene, decahydroheptalene, octahydroheptalene, hexahydroheptalene, and tetrahydroheptalene. In one embodiment, the $C_8$-$C_{12}$ bicyclic cycloalkyl group is substituted with one or more of the following groups: -halo, -0-($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_8$-$C_{12}$ bicyclic cycloalkenyl is unsubstituted.

The term "halo" as used herein refers to —F, —Cl, —Br or —I.

The term "3- to 7-membered monocyclic heterocycle" refers to: (i) a 3- or 4-membered non-aromatic monocyclic cycloalkyl in which 1 of the ring carbon atoms has been replaced with an NH, an O, or an S moiety; or (ii) a 5-, 6-, or 7-membered aromatic or non-aromatic monocyclic cycloalkyl in which 1-4 of the ring carbon atoms have been independently replaced with an NH, an O, or an S moiety. The non-aromatic 3- to 7-membered monocyclic heterocycles can be attached via a ring nitrogen, sulfur, or carbon atom. The aromatic 3- to 7-membered monocyclic heterocycles are attached via a ring carbon atom. Representative examples of a 3- to 7-membered monocyclic heterocycle group include, but are not limited to furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl, In one embodiment, the 3- to 7-membered monocyclic heterocycle group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the 3- to 7-membered monocyclic heterocycle is unsubstituted.

The term "8- to 12-membered bicyclic heterocycle" refers to a bicyclic 8- to 12-membered aromatic or non-aromatic bicyclic cycloalkyl in which one or both of the of the rings of the bicyclic ring system have 1-4 of its ring carbon atoms independently replaced with an NH, an O, or an S moiety. Included in this class are 3- to 7-membered monocyclic heterocycles that are fused to a benzene ring. A non-aromatic ring of an 8- to 12-membered monocyclic heterocycle is attached via a ring nitrogen, sulfur, or carbon atom. An aromatic 8- to 12-membered monocyclic heterocycles are attached via a ring carbon atom. Examples of 8- to 12-membered bicyclic heterocycles include, but are not limited to, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, cinnolinyl, decahydroquinolinyl, 1H-indazolyl, indolenyl, indolinyl, indolizinyl, indolyl, isobenzofuranyl, isoindazolyl, isoindolyl, isoindolinyl, isoquinolinyl, naphthyridinyl, octahydroisoquinolinyl, phthalazinyl, pteridinyl, purinyl, quinoxalinyl, tetrahydroisoquinolinyl, tetrahydroquinolinyl, and xanthenyl. In one embodiment, each ring of a the -8- to 12-membered bicyclic heterocycle group can substituted with one or more of the following groups: -halo, —O—($C_1$-$C_6$ alkyl), —OH, —CN, —COOR', —OC(O)R', —N(R')$_2$, —NHC(O)R'. or —C(O)NHR' groups wherein each R' is independently —H or unsubstituted —$C_1$-$C_6$ alkyl. Unless indicated, the 8- to 12-membered bicyclic heterocycle is unsubstituted. Representative examples of a "phenylene group" are depicted below:

The phrase "pharmaceutically acceptable salt," as used herein, is a salt of an acid and a basic nitrogen atom of a purine compound. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The pharmaceutically acceptable salt can also be a camphorsulfonate salt. The term "pharmaceutically acceptable salt" also refers to a salt of a purine compound having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine: mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. The term "pharmaceutically acceptable salt" also includes a hydrate of a purine compound.

Some chemical structures herein are depicted using bold and dashed lines to represent chemical bonds. These bold and dashed lines depict absolute stereochemistry. A bold line indicates that a substituent is above the plane of the carbon atom to which it is attached and a dashed line indicates that a substituent is below the plane of the carbon atom to which it is attached.

The term "effective amount" as used herein refers to an amount of a selective adenosine A1 agonist that is effective for: (i) treating or preventing elevated IOP; or (ii) reducing IOP in a human.

The term "subject" is intended to include organisms, e.g., prokaryotes and eukaryotes, which are capable of suffering from or afflicted with a disease, disorder or condition associated with elevated IOP. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from an increase in IOP. In another embodiment, the subject is a cell.

The term "treat," "treated," "treating" or "treatment" includes the diminishment or alleviation of at least one symptom associated or caused by the state, disorder or disease being treated. In certain embodiments, the treatment comprises the induction of elevated IOP, followed by the activation of the compound of the invention, which would in turn diminish or alleviate at least one symptom associated or caused by the elevated IOP. For example, treatment can be diminishment of one or several symptoms of a disorder or complete eradication of a disorder.

The term "use" includes any one or more of the following embodiments of the invention, respectively: the use in the treatment of elevated IOP; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from glaucoma, POAG or OHT.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

As used herein, the term "drop" refers to a quantity of ophthalmically acceptable fluid that resembles a liquid drop. In one embodiment, a drop refers to a liquid volume equivalent to about 5 µl to about 200 µl, e.g., about 30 µl to about 80 µl.

The following abbreviations are used herein and have the indicated definitions: CCPA is 2-chloro-N6-cyclopentyladenosine; CPA is N6-cyclopentyladenosine; NECA is adenosine-5'-(N-ethyl)carboxamido; NMR is nuclear magnetic resonance; R-PIA is N6-(2-phenyl-isopropyl) adenosine, R-isomer; OHT is ocular hypertension or POAG is primary open-angle glaucoma; HPβCD is hydroxypropyl β-cyclodextrin.

Methods of Synthesis

Compounds according to Formula I can be prepared by using synthetic procedures described in U.S. Pat. No. 7,423,144, the disclosure of which is incorporated herein in its entirety, as well as other published methods (see Cristalli et al., *J. Med. Chem.* 35:2363-2369, 1992; Cristalli et al., *J. Med. Chem.* 37:1720-1726, 1994; Cristalli et al, *J. Med. Chem.* 38:1462-1472, 1995; and Camaioni et al., *Bioorg. Med. Chem.* 5:2267-2275, 1997), or by using the synthetic procedures outlined below.

Scheme 1 shows methods for making nucleoside intermediates that are useful for making the compounds of the invention.

Scheme 1

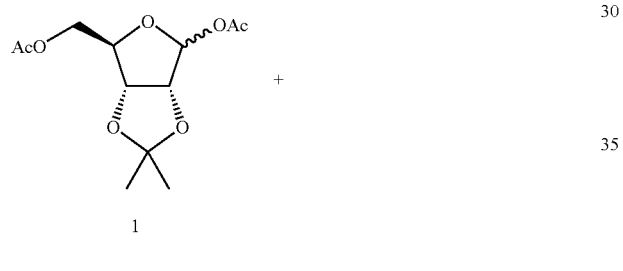

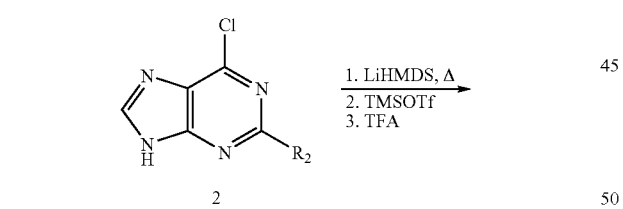

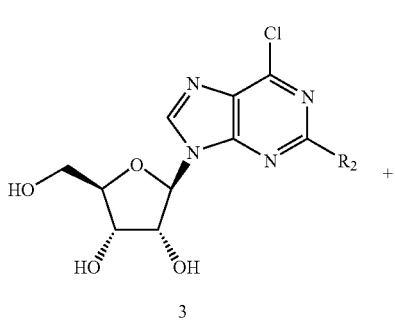

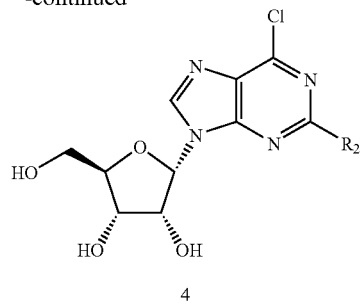

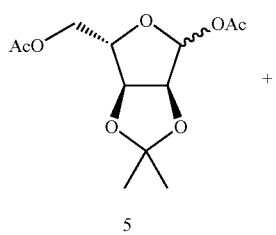

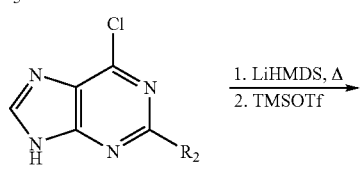

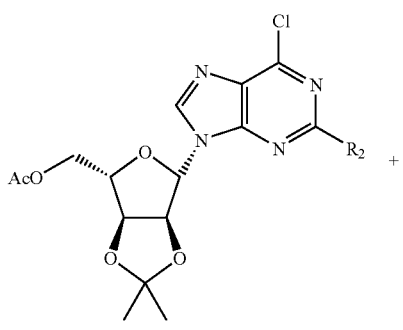

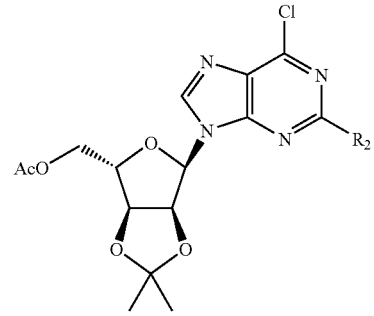

wherein $R_2$ is as defined above.

The protected ribose compound of Formula 1 can be coupled with a purine compound of Formula 2 using lithium hexamethyldisilazide and trimethylsilyl triflate, followed by acetonide removal using trifluoroacetic acid to provide nucleoside intermediates of Formula 3 and their corresponding other anomers of Formula 4. Similarly, the ribose diacetate of Formula 5 can be coupled with a compound of Formula 2 using lithium hexamethyldisilazide and trimethylsilyl triflate to provide acetonide-protected nucleoside intermediates of Formula 6 and their corresponding other anomers of Formula 7.

Scheme 2 shows a method useful for making the adenosine intermediates of Formula 8 which are useful for making the compounds of the invention.

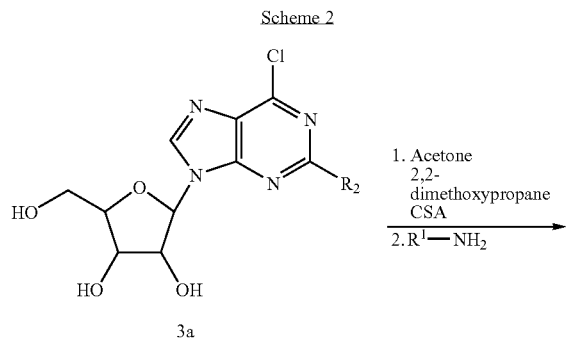

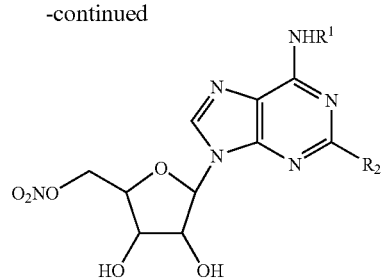

where $R^1$ and $R^2$ are defined above.

The adenosine intermediates of formula 8 can be converted to their 5'-nitrate analogs using nitric acid in the presence of acetic anhydride, or other nitrating agents, such as MsCl/ONO$_3$ or nitrosonium tetrafluoroborate. Acetonide removal using TFA/water provides compounds of the invention.

Methodology useful for making the Purine Derivatives of Formula (Id) wherein $R^3$ is —CH$_2$OSO$_3$H is outlined in Scheme 6.

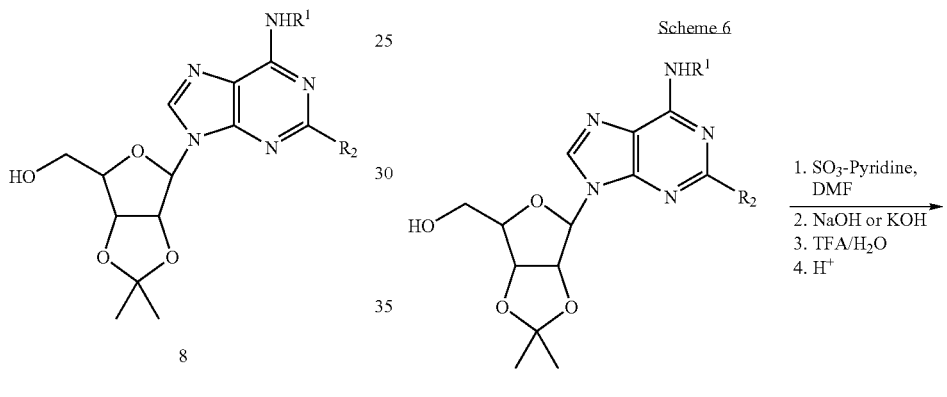

where $R^1$ and $R^2$ are defined above.

The 6-chloroadenosine derivative of formula 3a is converted to its 2',3'-acetonide using acetone and 2,2-dimethoxypropane in the presence of camphorsulfonic acid. The acetonide can be further derivatized using an amine of formula $R^1$—NH$_2$ in the presence of base to provide compounds of formula 8.

Methodology useful for making other compounds of the invention is described in Scheme 4.

where $R^1$ and $R^2$ are defined above.

The adenosine intermediates of formula 8 can be treated with sulfur trioxide-pyridine complex to provide the corresponding 5'-sulfonic acid pyridine salt intermediate. The pyridine salt intermediate can then be neutralized using NaOH or KOH, followed by acetonide removal using TFA/water to provide the corresponding sodium or potassium salt, respectively, of the Purine Derivatives of Formula (Id) wherein A is —CH$_2$OSO$_3$H. Treatment of the sodium or potassium salt with strong aqueous acid, such as sulfuric or hydrochloric acid, provides compounds of the invention wherein A is —CH$_2$OSO$_3$H.

Modes of Delivery

The compounds according to Formula I can be incorporated into various types of ophthalmic compositions or formulations for delivery. Formula I compounds may be delivered directly to the eye (for example: topical ocular drops or ointments; slow release devices such as pharmaceutical drug delivery sponges implanted in the cul-de-sac or implanted adjacent to the sclera or within the eye; periocular, conjunctival, sub-tenons, intracameral, intravitreal, or intracanalicular injections) or systemically (for example: orally, intravenous, subcutaneous or intramuscular injections; parenterally, dermal or nasal delivery) using techniques well known by those of ordinary skill in the art. It is further contemplated that the agents of the invention may be formulated in intraocular insert or implant devices.

The compounds of Formula I are preferably incorporated into topical ophthalmic formulations with a pH of about 4-8 for delivery to the eye. The compounds may be combined with opthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an opthalmologically acceptable surfactant to assist in dissolving the compound. Furthermore, the ophthalmic solution may contain an agent to increase viscosity or solubility such as hydroxypropyl β-Cyclodextrin (HPβCD), hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient may be combined with a preservative in an appropriate vehicle such as mineral oil, liquid lanolin, or white petrolatum. Sterile ophthalmic gel formulations may be prepared by suspending the compound in a hydrophilic base prepared from the combination of, for example, carbopol-974, or the like, according to the published formulations for analogous ophthalmic preparations; preservatives and tonicity agents can be incorporated.

Compounds in preferred embodiments are contained in a composition in amounts sufficient to lower IOP in patients experiencing elevated IOP and/or maintaining normal IOP levels in POAG or OHT patients. Such amounts are referred to herein as "an amount effective to control or reduce IOP," or more simply "an effective amount." The compounds will normally be contained in these formulations in an amount 0.05 mg/ml to 7.0 mg/ml but preferably in an amount of 0.4 to 7.0 mg/ml. Thus, for topical presentation 1 to 2 drops of these formulations would be delivered to the surface of the eye from 1 to 4 times per day, according to the discretion of a skilled clinician.

The compounds of Formula I can also be used in combination with other glaucoma treatment agents, such as, but not limited to, β-blockers, prostaglandin analogs, carbonic anhydrase inhibitors, $\alpha_2$ agonists, miotics, and neuroprotectants A3 antagonists, A2A agonists and combinations thereof.

Design of a Clinical Study Using Compounds of Formula I

The clinical study described herein is a multi-center, randomized, double-blind, placebo-controlled, dose-escalation study of a single topical ocular application of the study drug (i.e., Compound A or placebo) to the one study eye of adults with OHT or POAG. The "study eye" was defined as the eye with the higher mean IOP, recorded between 7:00 and 8:00 AM on the day prior to dosing (Day 0). Subject enrollment criteria included males and females with no childbearing potential, aged 18 to 75 years (inclusive), who signed informed consent, have been diagnosed with OHT or POAG, and had a low risk for acute exacerbation of their eye disease while enrolled.

The adult subjects were sequentially assigned to 1 of 7 treatment groups. Each treatment group included twelve subjects: 8 subjects randomized to receive 2.5, 7.5, 20, 60, 180, 350 or 700 micrograms of Compound A in the study eye and 4 randomized to receive matched placebo (see Table 1) on Day 1.

TABLE 1

Randomization Scheme in the Clinical Trial

|  | Study Eye | Non-Study Eye |
|---|---|---|
| Active (8 per treatment group) | Active drug (2.5-700 μg) | No treatment |
| Placebo (4 per treatment group) | Matched placebo | No treatment |

Masked-intraocular pressures were determined in duplicate with a Goldmann tonometer following traditional corneal anesthesia. Following determination of the bilateral baseline (predose) IOP measurements on the morning of Day 1, the assigned study drug (Compound A or matched placebo) was instilled as a single 50 μL drop to the one study eye only. Subsequent bilateral external eye examinations and masked-IOP determinations were performed at 9:00 AM, 10:00 AM, 12:00 noon, and 2:00 PM (each ±5 minutes), corresponding to 1, 2, 4, and 6 hours post study drug application. In addition in the 700 mcg cohort an IOP determination was performed at 6:00 PM (18:00), corresponding to 10 hours post study drug application.

Dosage/Dosage Form, Route, & Dose Regimen

Subjects had the study drug applied via eyedropper to the inferior conjunctival sac of the study eye. The study drug was only administered to one eye per subject (the study eye). Dosages ranged from 2.5 micrograms to 350 micrograms per 50 microliter drop, per respective treatment group. A board-certified ophthalmologist (or comparably trained designee) administered the study drug. Randomized enrollment of subjects into each successive treatment groups was predicated upon the review and approval of the safety data from the completed treatment groups by the Safety Research Committee, consisting of three qualified physicians (i.e., an internist, cardiologist, and ophthalmologist).

Formulation Example

Formulation is 1 mg of Compound A for every 20 mg of Hydroxypropyl β-Cyclodextrin (HPβCD) (i.e., 1:20 wt/wt) reconstituted with 0.9% Saline for Injection, USP, at concentrations indicated below.

| Clinical Dose (mcg/eye) | Compound A (mg/mL) | Ocular Dose Volume (μL) |
|---|---|---|
| 2.5 | 0.05 | 50 |
| 7.5 | 0.15 | 50 |
| 20 | 0.40 | 50 |
| 60 | 1.2 | 50 |
| 180 | 3.6 | 50 |
| 350 | 7.0 | 50 |
| 700 | 7.0 | 2 × 50 |

Results of the Clinical Trial

The results of the clinical trial are presented in the figures and further as described below.

The dose escalation scheme over the 7 treatment groups of the multi-center, randomized, double-blinded clinical study is shown in FIG. 1. Twelve subjects were randomly assigned to each treatment group: 8 subjects received Compound A and 4 subjects received placebo. Escalation to each successive treatment group was predicated upon the approval of the Safety Review Committee of the safety data from the most recently completed cohort.

Figure 2A:
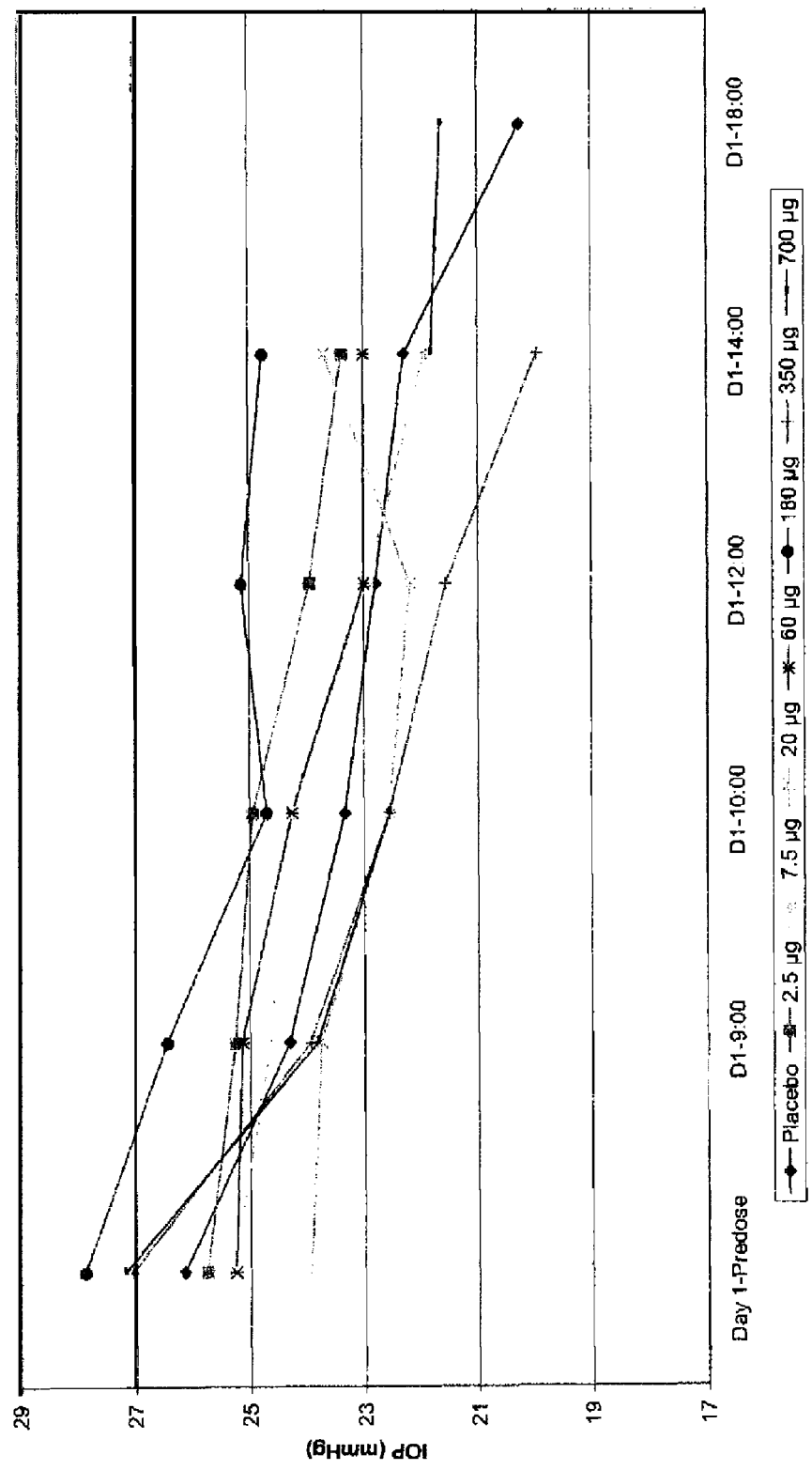
FIG. 2a shows the mean IOP (mmHg) in the study eye at each time point across all treatment groups.
Figure 2B:
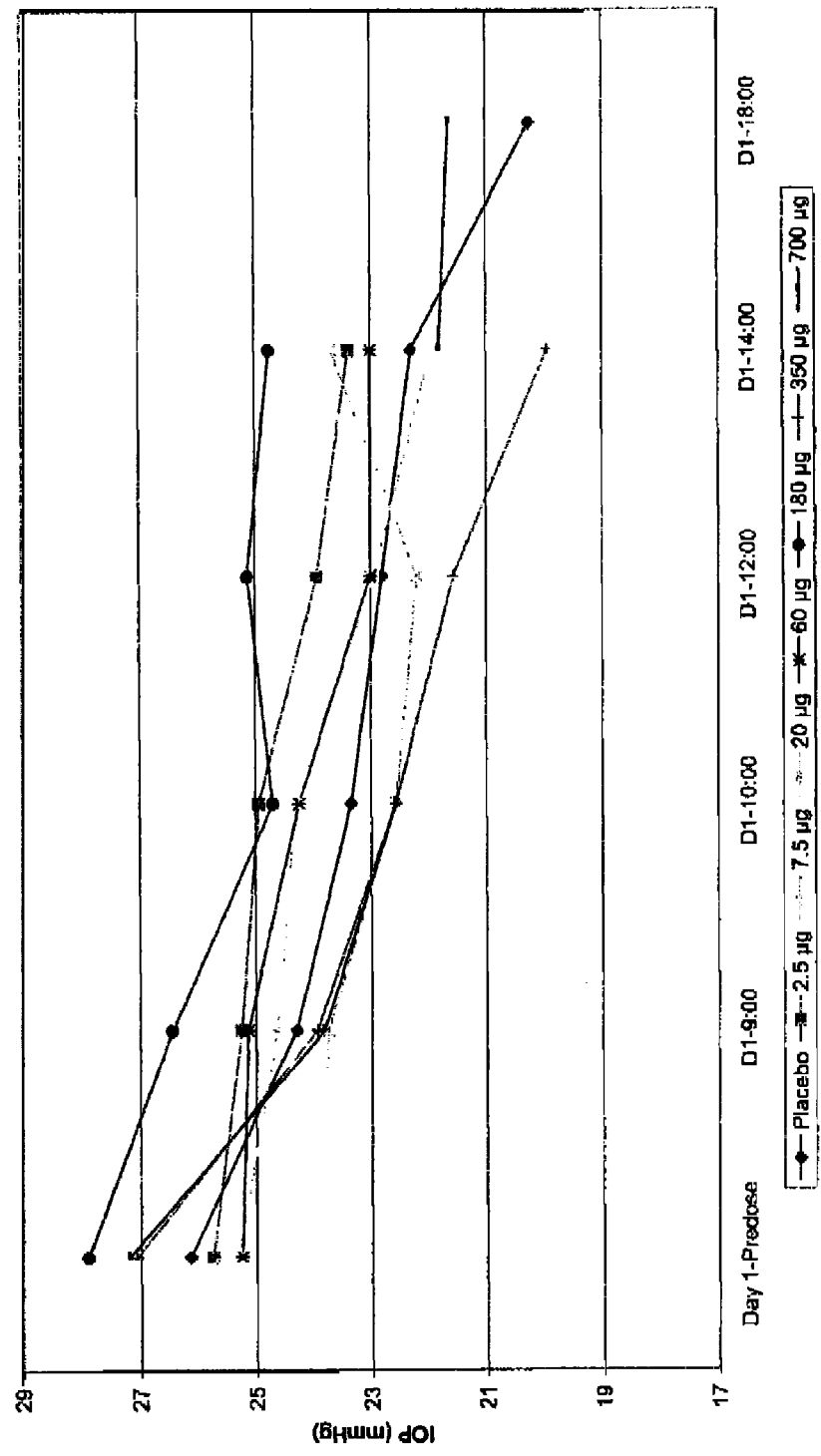
FIG. 2b shows the median IOP (mmHg) in the study eye across all treatment groups at each time point.
Figure 3A:
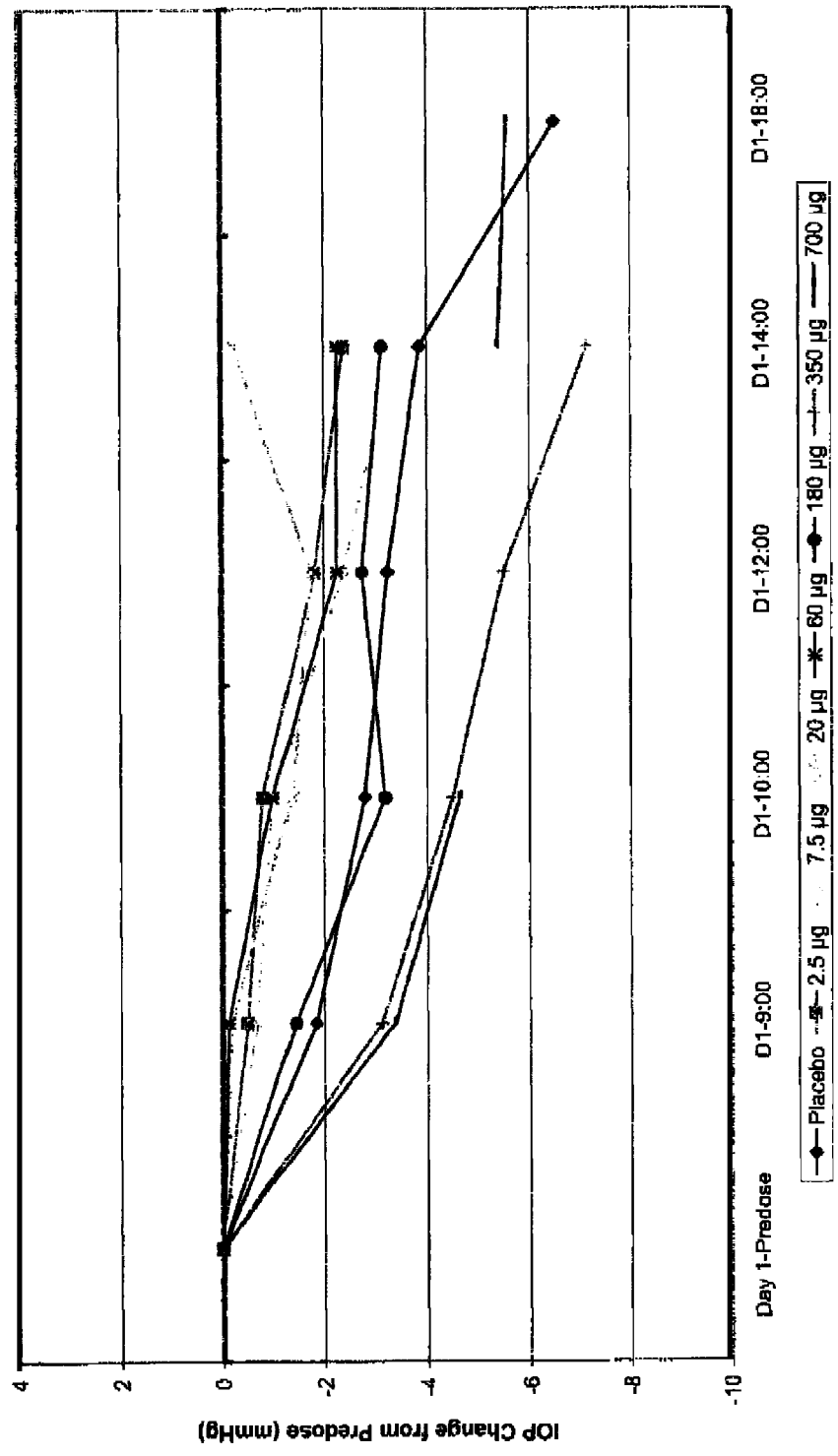
FIG. 3a shows the mean absolute IOP change from predose IOP (mmHg) in the study eye across all treatment groups at each time point.
Figure 3B:
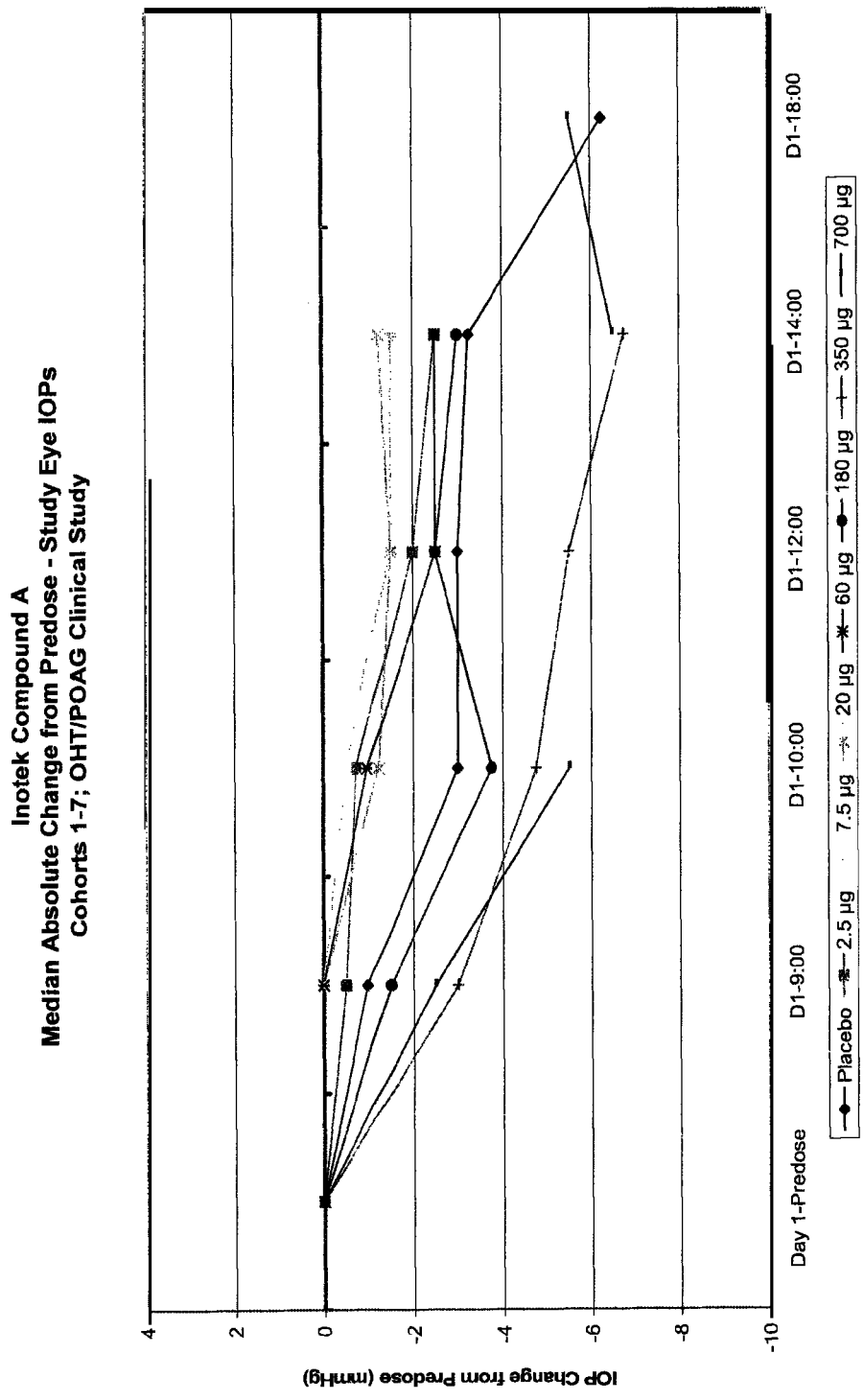
FIG. 3b shows the median absolute IOP change from predose IOP (mmHg) in the study eye across all treatment groups.

The mean and median IOP (mmHg) in the study eye at each time point across all treatment groups is shown in FIGS. 2a and 2b, respectively. The mean absolute and median absolute IOP change from predose IOP (mmHg) in the study eye across all treatment groups at each time point is shown in FIGS. 3a and 3b.

FIG. 4a presents a summary chart of the responder analysis in the 7 treatment groups at 10:00 AM. In human subjects treated with topical ocular doses of Compound A, at approximately 2 hours post-dose (approximately 10:00 AM), the largest portion of the difference in IOP between drug-treated and placebo-treated eyes is apparent. The 2 hours post-dose clinical IOP assessment is especially relevant for detecting the presence of an effect in human glaucoma/OHT patients with statistical significance.

FIG. 4b presents a summary chart of the responder analysis in the 7 treatment groups using the mean responder rate over a 6 hr postdose observation period. To obtain the response rate, the percent decrease in IOP for each subject at each of the 3 postdose time points were averaged. The mean of this percentage was used to determine the responder rate.

FIG. 5 presents the mean and median % decrease from baseline (BL; predose) and the categorical responder analysis of the 350 mcg cohort over the entire postdose observation period.

The figures presented in FIGS. 6 and 8 demonstrate the statistically significant decrease in the mean and median IOPs (from the predose baseline IOP determinations) observed in the 350 and 700 mcg cohorts relative to the placebo response.

FIG. 7 presents the mean and median % decrease from baseline (BL; predose) and the categorical responder analysis of the 700 mcg cohort over the postdose observation period.

Summary of Compound A Efficacy

Compound A was found to induce a decrement in IOP from the Day 1 pre-dose baseline that was:
1. Dose-related decrement in IOP
   a. A trend in the mean and median decrease in IOP and percent change from baseline was observed, especially at the 2 hours postdose time point. The largest mean and median decreases in IOP were found at the 350 mcg dose.
   b. The responder analysis showed a dose-response to Compound A in the numbers of subjects that achieved categorical mean decreases from baseline in IOP of ≧10%, ≧15% or ≧20%, throughout the observation period (~6 hrs). The % of subjects achieving greatest IOP decrement (responder analysis) was in the 350 mcg treatment group.
2. Statistically significant from placebo
   a. Statistically significant differences from the placebo response were observed in the 350 mcg and 700 mcg treatment groups at the 2 hours postdose time point.
3. In the 350 mcg treatment group, the decrease in IOP was found to last for the entire observation period (~6 hrs).

Synthesis Examples

2',3'-Isopropylidene-$N^6$-cyclohexyladenosine

A solution of 6-chloroadenosine (2.58 g) and cyclohexylamine (5 g) in ethanol (20 ml) was heated at reflux for 6 hours then cooled to room temperature. The reaction mixture was concentrated in vacuo and the resultant residue was diluted with water (50 ml) and ethyl acetate (300 ml). The organic layer was separated and the aqueous layer was extracted with ethyl acetate (2×50 ml). The combined organic layers were washed with water (1×30 ml), dried over sodium sulfate, concentrated in vacuo and dried under vacuum to provide $N^6$-cyclohexyladenosine as a white solid (2.600 g). $N^6$-Cyclohexyladenosine (2.6 g) was diluted with acetone (30 ml) and to the resultant solution was added 2,2-dimethoxypropane (12 ml), followed by D-camphorsulphonic acid (3.01 g) and the mixture was allowed to stir at room temperature for 18 hours. The reaction mixture was concentrated in vacuo and the resultant residue was diluted with ethyl acetate (150 ml), then neutralized to pH 8.0 using saturated aqueous $NaHCO_3$. The organic layer was separated, dried over sodium sulfate, concentrated in vacuo. The residue was purified twice on the silica gel column using MeOH—$CH_2Cl_2$ (4:96) as an eluent to provide 2',3'-isopropylidene-$N^6$-cyclohexyladenosine (3.16 g). $^1$H NMR ($CDCl_3$): δ 1.23-1.47 (m, 9H), 1.38 (s, 3H), 1.64 (s, 3H), 1.79-1.81 (m, 1H), 2.04-2.06 (m, 1H), 3.80 (d, J=12 Hz, 1H), 3.96 (d, J=12 Hz, 1H), 4.53 (s, 1H), 5.09-5.16 (m, 2H), 5.80-5.92 (m, 2H), 7.79 (s, 1H), 8.24 (s, 1H), 8.22-8.38 (m, 1H).

$N^6$-Cyclohexyladenosine-5'-O-nitrate (Compound E)

Acetic anhydride (6 ml) was slowly added to a stirred solution of nitric acid (2 g, 63%) at −25° C. ($CCl_4$-$CO_2$ bath used for cooling) and the reaction temperature maintained at −7.5 to 0° C. for additional 1 hr. A solution of 2',3'-isopropylidene-$N^6$-cyclohexyladenosine (1.0 g) in acetic anhydride (3 mL) was added slowly. The resultant reaction was allowed to stir at 0 to −5° C. for 2 hour and the mixture was slowly poured slowly into an ice-cold solution of aqueous $NaHCO_3$ (40 mL) and ethyl acetate (150 mL) and it was allowed to stir for 5 minutes. The organic layer was separated and washed with water, dried over sodium sulfate, and concentrated in vacuo. The residue was diluted with a mixture of TFA (16 mL) and water (4 mL) and the mixture was allowed to stir for 30 minutes at room temperature. The mixture was concentrated in vacuo and the resultant residue was diluted with water (10 mL) and concentrated in vacuo. The residue obtained was diluted with ethyl acetate and washed with saturated aqueous sodium bicarbonate, and the organic layer was dried over sodium sulfate and concentrated in vacuo. The residue was purified on the silica gel column using ethyl acetate hexane (from 40:60 to 20:80 gradient) to provide $N^6$-cyclohexyladenosine-5'-O-nitrate (0.150 gm). $^1$H NMR (DMSO-$D_6$): δ 1.08-1.13 (m, 1H), 1.27-1.41 (m, 4H), 1.57-1.83 (m. 6H), 4.12-4.17 (m, 2H), 4.30-4.33 (m, 1H), 5.48 (d, J=5.4 Hz, 1H), 5.60 (d, J=5.7 Hz, 1H), 5.90 (d, J=4.8 Hz, 1H), 7.59 (d, J=8.1 Hz, 1H), 8.16 (s, 1H), 8.29 (s, 1H).

$N^6$-(exo-2-Norbornyl)adenosine-5'-O-nitrate (Compound F)

2',3'-Isopropylidene-$N^6$-exo-norbornyladenosine was prepared following the procedure of 2',3'-isopropylidene-$N^6$-cyclohexyladenosine and used for the subsequent reaction. Acetic anhydride (6 ml) was slowly added to a stirred solution of nitric acid (2 g, 63%) at −25° C. ($CCl_4$-$CO_2$ bath used for cooling) and the reaction temperature maintained at −7.5 to 0° C. for additional 1 hr. A solution of 2',3'-isopropylidene-$N^6$-exo-norbornyladenosine (1.2 g) in acetic anhydride (3 mL) was added slowly. The mixture was allowed to stir at 0 to −5° C. for 40 minutes and the mixture was slowly poured slowly into an ice-cold solution of aqueous NaHCO$_3$ (40 mL). The solution was extracted in dichloromethane. The organic layer was separated and washed with brine, dried over sodium sulfate, and concentrated under vacuo. The residue was purified on the silica gel column using ethyl acetate-hexane (1:1) to provide the desired product (0.245 g) and the starting compound (1.0 g). The nitro product (0.245 g) was diluted in a mixture of TFA (15 mL) and water (5 mL) and the mixture was allowed to stir for 30 minutes at room temperature. It was concentrated under vacuo and diluted with water (10 mL) and concentrated in vacuo. The resultant residue was diluted with ethyl acetate and washed with saturated aqueous sodium bicarbonate. The organic layer was dried over sodium sulfate and concentrated in vacuo. The residue was recrystallized from the mixture of ethyl acetate and hexane to provide N$^6$-exo-2-norbornyladenosine-5'-O-nitrate (0.123 gm). $^1$H NMR (DMSO-D$_6$): δ 1.03-1.21 (m, 3H), 1.40-1.56 (m, 3H), 1.58-1.64 (m. 4H), 3.94 (bs, 1H), 4.13-4.17 (m, 1H), 4.30 (bs, 1H), 4.66-4.87 (m, 3H), 5.49 (d, J=5.4 Hz, 1H), 5.62 (d, J=5.4 Hz, 1H), 5.91 (d, J=4.8 Hz, 1H), 7.60 (d, J=6.6 Hz, 1H), 8.20 (s, 1H), 8.31 (s, 1H).

2-Chloro-N$^6$-cyclohexyladenosine

A mixture of 2,6-dichloroadenosine (1.0 g) and cyclohexylamine (0.926 g) in ethanol (30 ml) was heated at reflux for 6 hours then cooled to room temperature. The mixture was concentrated under vacuo. The residue was purified on the silica gel column using MeOH—CH$_2$Cl$_2$ (1:6 to 1:5). The combined fractions were concentrated and dried under vacuum to provide 2-chloro-N$^6$-cyclohexyladenosine as a white solid (2.600 g). $^1$H NMR (DMSO-D$_6$): δ 1.12-1.21 (m, 2H), 1.33-1.43 (m, 3H), 1.63-1.86 (m, 6H), 3.57-3.62 (m, 1H), 3.66-3.69 (m, 1H), 3.97 (d, J=3 Hz, 1H), 4.16 (d, J=3.3 Hz, 1H), 4.54 (d, J=5.4 Hz, 1H), 5.08-5.11 (m, 1H), 5.24 (d, J=4.8 Hz, 1H), 5.51 (d, J=5.7 Hz, 1H), 5.85 (d, J=5.7 Hz, 1H), 8.26 (d, J=8.4 Hz, 1H), 8.41 (s, 1H).

2-Chloro-2',3'-isopropylidene-N$^6$-cyclohexyladenosine

2-Chloro-N$^6$-cyclohexyladenosine (0.5 g) was diluted with acetone (30 ml) and to the mixture was added 2,2-dimethoxypropane (2.04 g), followed by D-camphorsulphonic acid (CSA, 0.272 g). The resultant reaction mixture was allowed to stir at room temperature for 2 hours. Additional CSA (0.2 g) was added and stirred for 2 hours. The mixture was concentrated in vacuo and the resultant residue was diluted with ethyl acetate, then neutralized to pH 8.0 using concentrated aqueous NaHCO$_3$. The organic layer was separated, dried over sodium sulfate, concentrated under vacuum to provide 2-chloro-2',3'-isopropylidene-N$^6$-cyclohexyladenosine (0.378 g). $^1$H NMR (CDCl$_3$): δ 1.23-1.30 (m, 3H), 1.36-1.44 (m, 1H), 1.63 (s, 3H), 1.68-1.79 (m, 5H), 2.04-2.08 (m, 2H), 3.81 (d, J=5 Hz, 1H), 3.99 (d, J=12.9 Hz, 1H), 4.51 (s, 1H), 5.11 (d, J=5.7 Hz, 1H), 5.15-5.18 (m, 1H), 5.75 (bs, 1H), 5.78 (d, J=4.5 Hz, 1H), 5.96 (bs, 1H), 7.76 (s, 1H).

2-Chloro-N$^6$-cyclohexyladenosine-5'-O-sulfate sodium salt (Compound G)

2-Chloro-2',3'-isopropylidene-N$^6$-cyclohexyladenosine (0.540 g) was dissolved in DMF (6 ml) and added slowly in to the solution of sulfur trioxide (0.302 g) in DMF (3 ml). The mixture was stirred overnight at room temperature. It was concentrated on ratavaporator and the residue was diluted with water (8 ml). The water solution was slowly neutralized with NaOH (0.1N) to pH 7.0. It was extracted in ethyl acetate and the aqueous layer was then concentrated. The white solid obtained was used as such for the next step. The protected sodium sulfate salt was treated with the mixture of TFA-water (16:4 ml) and stirred for 30 min. The reaction mixture was concentrated and the residue was crystallized from acetone to provide 2-chloro-N$^6$-cyclohexyladenosine-5'-O-sulfate sodium salt (0.150 g). $^1$H NMR (DMSO-D$_6$): δ 1.10-1.13 (m, 1H), 1.25-1.41 (m, 4H), 1.57-1.83 (m. 6H), 3.72-4.08 (m, 4H), 4.47 (s, 1H), 5.81 (s, 1H), 8.14 (d, J=6.0 Hz, 1H), 8.43 (s, 1H).

2-Chloro-N$^6$-cyclohexyladenosine-5'-O-nitrate (Compound H)

Following the nitration and the TFA water deprotection reactions, 2-chloro-N$^6$-cyclohexyladenosine-5'-O-nitrate was prepared from 2-chloro-2',3'-isopropylidene-N$^6$-cyclohexyladenosine. $^1$H NMR (CDCl$_3$): δ 1.06-1.42 (m, 4H), 1.64-1.88 (m, 5H), 4.08 (bs, 1H), 4.21 (s, 1H), 4.30 (d, J=4.2 Hz, 1H), 4.41 (s, 1H), 4.83-4.88 (m, 2H), 5.57 (d, J=5.4 Hz, 1H), 5.70 (d, J=4.5 Hz, 1H), 5.90 (d, J=5.1 Hz, 1H), 8.26 (d, J=8.7 Hz, 1H), 8.38 (s, 1H).

Synthesis of Compound A

N$^6$-Cyclopentyladenosine

A solution of 6-chloroadenosine (43 g) and cyclopentylamine (5 eq.) in ethanol (50 eq.) was heated at reflux for 3 hours then cooled to room temperature. The resultant reaction mixture was concentrated in vacuo and the resultant residue was diluted with water (400 ml) and ethyl acetate (400 ml). The organic layer was separated and the aqueous layer was extracted into ethyl acetate (2×400 ml). The combined organic layers were washed with water (2×200 ml), dried over sodium sulfate, concentrated in vacuo and dried under vacuum to provide a solid which was suspended in MeOH (400 mL), filtered and dried to provide N$^6$-cyclopentyladenosine (43.8 g).

2',3'-isopropylidene-N$^6$-cyclopentyladenosine

N$^6$-cyclopentyladenosine (43 g) was diluted with acetone (75 eq.) and to the resultant solution was added 2,2-dimethoxypropane (5 eq.), followed by D-camphorsulphonic acid (1 eq) and the resultant reaction was allowed to stir at room temperature for 3 hours. The resultant reaction mixture was concentrated in vacuo and the resultant residue was diluted with ethyl acetate, then neutralized to pH 7.0 using concentrated aqueous NaHCO$_3$. The organic layer was separated, dried over sodium sulfate, concentrated in vacuo and dried under vacuum to provide a solid which was suspended in hexane (250 mL), filtered, washed with hexane and dried under vacuum to provide 2',3'-isopropylidene-N$^6$-cyclopentyl adenosine (43 g).

2',3'-isopropylidene-N$^6$-cyclopentyladenosine-5'-nitrate

Acetic anhydride (22 eq) was slowly added to a stirred solution of nitric acid (5 eq., 63%) at −10° C. (acetonitrile-CO$_2$ bath used for cooling) over a period of 4 hours with the reaction temperature maintained at −5 to 5° C. during the addition. The resultant solution was cooled to −20° C. and a solution of 2',3'-isopropylidene-N$^6$-cyclopentyladenosine (18.250 gm, 0.048 mol) in acetic anhydride (37 mL, 8 eq.) was added slowly. The resultant reaction was allowed to stir at −15 to −5° C. for 1 hour and the resultant reaction mixture was slowly poured slowly into an ice-cold solution of aqueous NaHCO$_3$ (168 gm in 800 mL water) and ethyl acetate (350 mL) and the resultant solution was allowed to stir for 5 minutes. The organic layer was separated and the aqueous layer was extracted using ethyl acetate (350 mL). The combined organic layers were washed with water, and dried over sodium sulfate, concentrated in vacuo and purified using flash column chromatography on silica gel using 70% ethyl acetate-hexane as eluent to provide 2',3'-isopropylidene-N$^6$-cyclopentyladenosine-5'-nitrate (14.9 g).

Compound A

2',3'-isopropylidene-N$^6$-cyclopentyladenosine-5'-nitrate (4.8 g) was diluted with a mixture of TFA (20 mL) and water (5 mL) and the resultant reaction was allowed to stir for 30 minutes at room temperature. The resultant reaction mixture was concentrated in vacuo and the resultant residue was diluted with water (10 mL) and concentrated in vacuo. The resultant residue was diluted with ethyl acetate and washed with saturated aqueous sodium bicarbonate, and the organic layer was dried over sodium sulfate and concentrated in vacuo to provide a white solid residue which was dried under vacuum and then recrystallized from cold ethanol to provide Compound A (3.1 gm). $^1$H-NMR (DMSO-d$_6$): δ 1.49-1.58 (m, 4H), 1.66-1.72 (m, 2H), 1.89-1.94 (m, 2H), 4.12-4.17 (m, 1H), 4.28-4.33 (m, 1H), 4.48 (bs, 1H), 4.65-4.87 (m, 3H), 5.5 (d, J=5.1 Hz, 1H), 5.63 (d, J=5.7 Hz, 1H), 5.91 (d, J=5.1 Hz, 1H), 7.75 (d, J=7.5 Hz, 1H), 8.17 (bs, 1H), 8.30 (s, 1H); MS (ES$^+$): m/z 381.35 (M+1); Anal. Calcd for $C_{15}H_{20}N_6O_6$: C, 47.37; H, 5.30; N, 22.10. Found: C, 47.49; H, 5.12; N, 21.96.

Synthesis of Compound B

2-Chloro-N$^6$-cyclopentyladenosine

2',3',5'-triacetoxy-2,6-dichloroadenosine (1.5 g) and cyclopentylamine (8 eq.) were diluted with ethanol (50 eq.) and the resulting solution was heated at reflux for about 15 hours, then cooled to room temperature and concentrated in vacuo to provide a crude residue which was diluted with a mixture of ethyl acetate and water and transferred to a separatory funnel. The organic layer was separated, dried over sodium sulfate and concentrated in vacuo to provide a crude residue which was purified using flash column chromatography on silica gel (8% MeOH-dichloromethane as eluent) to provide 2-chloro-N$^6$-cyclopentyladenosine (0.948 g). MS m/z 370.32 [M+H]$^+$.

2',3'-Isopropylidene-2-chloro-N$^6$-cyclopentyladenosine 2-chloro-N$^6$-cyclopentyladenosine (900 mg, as prepared in the previous step) and 2,2-dimethoxypropane (10 eq.) were diluted with acetone (15 mL) and to the resulting solution was added D-camphorsulphonic acid (1 eq) and the resulting reaction was allowed to stir at room temperature for 2 hr. The resulting reaction mixture was concentrated in vacuo, diluted with a mixture of saturated aqueous NaHCO$_3$ and ethyl acetate, and transferred to a separatory funnel. The organic layer was separated, dried over sodium sulfate and concentrated in vacuo to provide a crude residue which was purified using flash column chromatography on silica gel (using 5% MeOH-dichloromethane as eluent) to provide 2',3'-Isopropylidene-2-chloro-N$^6$-cyclopentyladenosine (0.905 g). $^1$H NMR (CDCl$_3$, 300 MHz): δ 1.36 (s, 3H), 1.62 (s, 3H), 1.66-2.16 (m, 9H), 3.78 (d, J=12.9 Hz, 1H), 3.98 (d, J=12.9 Hz, 1H), 4.51 (bs, 1H), 4.55-4.60 (m, 1H), 5.09-5.17 (m, 2H), 5.81 (bs, 1H), 7.25 (s, 1H), 7.89 (s, 1H).

2',3'-Isopropylidene-2-chloro-N$^6$-cyclopentyladenosine-5'-nitrate

A solution of nitric acid (2.0 mL, 60%) was added slowly over a period of 30 minutes to acetic anhydride (16.0 mL) at −10 to 10° C. (using acetonitrile-CO$_2$ cooling bath) and the reaction mixture was allowed to stir at −10 to 10° C. for 10 minutes. The reaction mixture was then cooled to −30° C. and then a solution of 2',3'-Isopropylidene-2-chloro-N$^6$-cyclopentyladenosine (655 mg, 0.0016 mol, as prepared in the previous step) in acetic anhydride (8.0 mL) was added slowly. When addition was complete, the resulting reaction was allowed to warm to −5° C. and monitored using TLC (solvent 5% MeOH—CH$_2$Cl$_2$ or 70% EtOAc-hexane). When the reaction was complete, the reaction mixture was poured slowly into an ice cold mixture of saturated aqueous NaHCO$_3$ (300 equivalent in 75 mL water) and ethyl acetate (60 mL). The organic layer was separated and the aqueous layer was back extracted with ethyl acetate. The combined organic layers were washed with water, dried over sodium sulfate, and concentrated in vacuo to provide a crude residue. The crude residue was purified using flash column column (5% methanol-dichloromethane as eluent) to provide 2',3'-Isopropylidene-2-chloro-N$^6$-cyclopentyladenosine-5'-nitrate (0.435 g). $^1$H NMR (CDCl$_3$, 300 MHz): δ 1.38 (s, 3H), 1.59 (s, 3H), 1.66-2.13 (m, 9H), 4.50-4.55 (m, 1H), 4.71-4.83 (m, 2H), 5.14-5.17 (m, 1H), 5.31 (d, J=5.7 Hz, 1H), 6.04 (s, 1H), 7.24 (s, 1H), 7.81 (s, 1H). MS m/z 455.44 [M+H]$^+$.

Compound B

2',3'-Isopropylidene-2-chloro-N$^6$-cyclopentyladenosine-5'-nitrate (0.435 g, as prepared in the previous step) was diluted with TFA (20 mL) and water (5 mL) and the resulting solution was allowed to stir for 30 minutes. The resulting reaction mixture was concentrated in vacuo and the resulting residue was diluted with water (10 mL) and the resulting solution was concentrated in vacuo. The crude residue obtained was diluted with ethyl acetate, transferred to a separatory funnel, washed with saturated aqueous sodium bicarbonate, dried over sodium sulfate and concentrated in vacuo. The crude residue obtained was purified using flash column chromatography on silica gel (using 10% methanol-dichloromethane as eluent) to provide Compound 16 (0.250 g). $^1$H NMR (DMSO-d$_6$, 300 MHz): δ 1.52-1.95 (m, 9H), 4.13-4.24 (m, 2H), 4.55-4.58 (m, 1H), 4.73-4.85 (m, 2H), 5.50 (bs, 1H), 5.61 (bs, 1H), 5.84 (d, J=5.1 Hz, 1H), 8.33 (bs, 2H) MS m/z 414.85 [M+H]$^+$.

Synthesis of Compound C

Sodium Salt

A mixture of 2',3'-isopropylidene-N$^6$-cyclopentyladenosine (1 g, 0.0026 mol, prepared as set forth in Example 1) and sulfur trioxide-pyridine complex (0.0039 mol) in DMF (17 mL) was stirred at room temperature for about 18 hours. The DMF was removed in vacuo and the resulting residue was dried in vacuo. The dried residue was diluted with water (25 mL), neutralized to pH 7.0 using NaOH (1N) and concentrated in vacuo to provide a crude residue which was diluted with an solution of TFA (80% solution in water, 50 mL). The resulting solution was allowed to stir at 25° C. for 30 minutes and the reaction mixture was concentrated in vacuo to afford a crude residue which was diluted with water (10 mL) and concentrated in vacuo. The crude compound obtained was recrystallized from acetone-water to provide compound C (sodium salt) (805 mg). $^1$HMNR (DMSO-d$_6$, 300 MHz): 1.53-1.96 (m, 9H), 3.78-4.10 (m, 4H), 4.43-4.54 (m, 2H), 5.90 (d, J=5.1 Hz, 1H), 8.23 (s, 1H), 8.46 (s, 1H). MS m/z 416.20 [M+H]$^+$.

Example

Binding Studies

Cell Culture and Membrane Preparation

CHO cells stably transfected with human adenosine A$_1$ receptor are grown and maintained in Dulbecco's Modified Eagles Medium with nutrient mixture F12 (DMEM/F12) without nucleosides, containing 10% fetal calf serum, penicillin (100 U/mL), streptomycin (100 µg/mL), L-glutamine (2 mM) and Geneticin (G-418, 0.2 mg/mL; A$_{2B}$, 0.5 mg/mL) at 37° C. in 5% CO$_2$/95% air. Cells are then split 2 or 3 times weekly at a ratio of between 1:5 and 1:20.

Membranes for radioligand binding experiments are prepared from fresh or frozen cells as described in Klotz et al., *Naunyn-Schmiedeberg's Arch. Pharmacol*, 357:1-9 (1998). The cell suspension is then homogenized in ice-cold hypotonic buffer (5 mM Tris/HCl, 2 mM EDTA, pH 7.4) and the homogenate is spun for 10 minutes (4° C.) at 1,000 g. The membranes are then sedimented from the supernatant for 30 minutes at 100,000 g and resuspended in 50 mM Tris/HCl buffer pH 7.4 (for A$_3$ adenosine receptors: 50 mM Tris/HCl, 10 mM MgCl$_2$, 1 mM EDTA, pH 8.25), frozen in liquid nitrogen at a protein concentration of 1-3 mg/mL and stored at −80° C.

Adenosine Receptor Binding Studies

The affinities of selected Purine Compounds for the adenosine A$_1$ receptor can be determined by measuring the displacement of specific [$^3$H] 2-chloro-N$^6$-cyclopentyl adenosine binding in CHO cells stably transfected with human recombinant A$_1$ adenosine receptor expressed as Ki (nM).

Dissociation constants of unlabeled compounds (K$_i$-values) are determined in competition experiments in 96-well microplates using the A$_1$ selective agonist 2-chloro-N$^6$-[$^3$H] cyclopentyladenosine ([$^3$H]CCPA, 1 nM) for the characterization of A$_1$ receptor binding. Nonspecific binding is determined in the presence of 100 µM R-PM and 1 mM theophylline, respectively. For details see Klotz et al., *Naunyn-Schmiedeberg's Arch. Pharmacol.*, 357:1-9, 1998. Binding data can be calculated by non-linear curve fitting using the program SCTFIT (De Lean et al. *Mol. Pharm.* 1982, 21:5-16).

Functional Characterization

The A$_1$ and A$_3$ receptor-mediated inhibition of forskolin-stimulated adenylyl cyclase activity was tested in membranes prepared from CHO cells stably transfected with the human A$_1$ and A$_3$ adenosine receptors. The A$_{2a}$ and A$_{2b}$ receptor-mediated stimulation of basal cyclase activity was tested in membranes prepared from CHO cells stably transfected with the human A$_{2a}$ and A$_3$ adenosine receptors Adenylyl Cyclase Inhibition Via Human Adenosine A$_1$ and A$_3$ Receptors

| | A$_1$ (EC$_{50}$ nM) | A$_3$ (EC$_{50}$ nM) |
|---|---|---|
| Compound A | 17 | >100,000 |
| Compound B | 20 | >100,000 |
| Compound E | 29 | >100,000 |
| Compound G | 19 | >100,000 |

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. A method of reducing intraocular pressure (IOP) in a human in need thereof, comprising the step of: applying an effective amount of a compound according to Formula I or a pharmaceutically acceptable salt thereof, to an affected eye of a human,

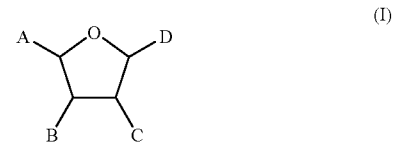

wherein
A is —CH$_2$ONO$_2$, —CH$_2$OSO$_3$Na or —CH$_2$OSO$_3$H;
B and C are —OH;
D is

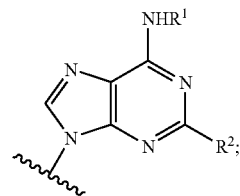

A and B are trans with respect to each other;
B and C are cis with respect to each other;
C and D are cis or trans with respect to each other;
R$^1$ is —H, —C$_1$-C$_{10}$ alkyl, -aryl, -3- to 7-membered monocyclic heterocyclyl, 8 to 12-membered bicyclic heterocyclyl, C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl —(CH$_2$)$_n$—(C$_3$-C$_8$ monocyclic cycloalkyl), —(CH₂)ₙ—(C₃-C₈ monocyclic cycloalkenyl), —(CH₂)ₙ—(C₈-C₁₂ bicyclic cycloalkyl), —(CH₂)ₙ—(C₈-C₁₂ bicyclic cycloalkenyl), or —(CH₂)ₙ-aryl;

R² is —H, halo, —CN, —NHR⁴, —NHC(O)R⁴, —NHC(O)OR⁴, —NHC(O)NHR⁴, —NHNHC(O)R⁴, —NHNHC(O)OR⁴, —NHNHC(O)NHR⁴, or —NH—N=C(R⁶)R⁷;

R⁴ is —C₁-C₁₅ alkyl, -aryl, —(CH₂)ₙ-aryl, —(CH₂)ₙ-(3- to 7-membered monocyclic heterocyclyl), (CH₂)ₙ-(8- to 12-membered bicyclic heterocyclyl), (CH₂)ₙ—(C₃-C₈ monocyclic cycloalkyl), —(CH₂)ₙ—(C₃-C₈ monocyclic cycloalkenyl), —(CH₂)ₙ—(C₈-C₁₂ bicyclic cycloalkyl), —(CH₂)ₙ—(C₈-C₁₂ bicyclic cycloalkenyl), —C≡C—(C₁-C₁₀ alkyl) or —C≡C-aryl;

R⁶ is —C₁-C₁₀ alkyl, -aryl, —(CH₂)ₙ-aryl, —(CH₂)ₙ-(3- to 7-membered monocyclic heterocyclyl), (CH₂)ₙ-(8- to 12-membered bicyclic heterocyclyl), (CH₂)ₙ—(C₃-C₈ monocyclic cycloalkyl), —(CH₂)ₙ—(C₃-C₈ monocyclic cycloalkenyl), —(CH₂)ₙ—(C₈-C₁₂ bicyclic cycloalkyl), —(CH₂)ₙ—(C₈-C₁₂ bicyclic cycloalkenyl), —(CH₂)ₙ—(C₃-C₈ monocyclic cycloalkenyl), -phenylene-(CH₂)ₙCOOH, or -phenylene-(CH₂)ₙCOO—(C₁-C₁₀ alkyl);

R⁷ is —H, —C₁-C₁₀ alkyl, -aryl, —(CH₂)ₙ-aryl, —(CH₂)ₙ-(3- to 7-membered monocyclic heterocyclyl), (CH₂)ₙ-(8- to 12-membered bicyclic heterocyclyl), (CH₂)ₙ—(C₃-C₈ monocyclic cycloalkyl), —(CH₂)ₙ—(C₃-C₈ monocyclic cycloalkenyl), —(CH₂)ₙ—(C₈-C₁₂ bicyclic cycloalkenyl) or —(CH₂)ₙ—(C₈-C₁₂ bicyclic cycloalkyl);

wherein -3- to 7-membered monocyclic heterocyclyl is a 3- or 4-membered non-aromatic monocyclic cycloalkyl in which 1 of the ring carbons has been replaced with an NH, an O, or an S moiety; or a 5-, 6-, or 7-membered aromatic or non-aromatic monocyclic cycloalkyl in which 1-4 of the ring carbons have been independently replaced with an NH, an O, or an S moiety, wherein -8- to 12-membered bicyclic heterocyclyl is a bicyclic 8- to 12-membered aromatic or non-aromatic bicyclic cycloalkyl in which one or both of the rings of the bicyclic ring system have 1-4 of its ring carbons independently replaced with an NH, an O, or an S moiety, and each n is independently an integer ranging from 1 to 5, and a pharmaceutically acceptable vehicle.

2. The method of claim 1, wherein the compound of Formula I has the formula:

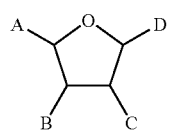

(Ib)

or a pharmaceutically acceptable salt thereof,
wherein
A is —CH₂ONO₂;
B and C are —OH;
D is

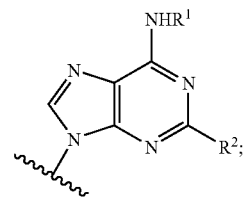

A and B are trans with respect to each other;
B and C are cis with respect to each other;
C and D are cis or trans with respect to each other;
R¹ is —C₃-C₈ monocyclic cycloalkyl, -3- to 7-membered monocyclic heterocyclyl or —C₈-C₁₂ bicyclic cycloalkyl; and
R² is —H or -halo.

3. The method as claimed in claim 1 wherein the compound of Formula I is selected from the group consisting of:

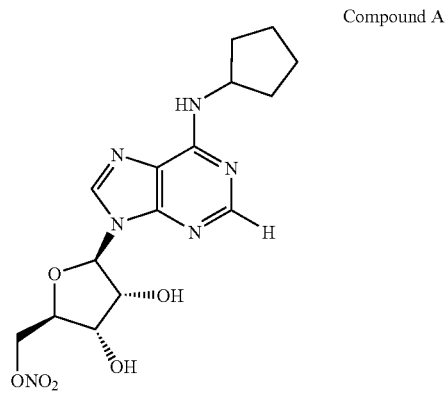

((2R,3S,4R,5R)-5-(6-(cyclopentylamino)-9H-purin-9-yl)-3,4-dihydroxytetrahydrofuran-2-yl)methyl nitrate,

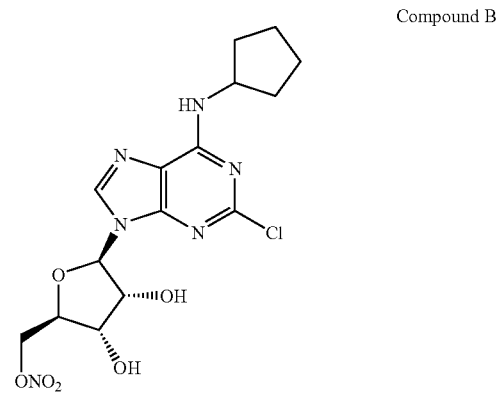

33

((2R,3S,4R,5R)-5-(2-chloro-6-(cyclopentylamino)-9H-purin-9-yl)-3,4-dihydroxytetrahydrofuran-2-yl)methyl nitrate, Compound C

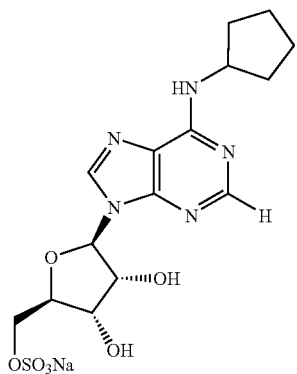

sodium ((2R,3S,4R,5R)-5-(6-(cyclopentylamino)-9H-purin-9-yl)-3,4-dihydroxytetrahydrofuran-2-yl)methyl sulfate, Compound D

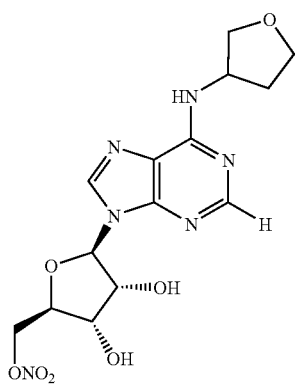

((2R,3S,4R,5R)-3,4-dihydroxy-5-(6-(tetrahydrofuran-3-ylamino)-9H-purin-9-yl)tetrahydrofuran-2-yl)methyl nitrate, Compound E

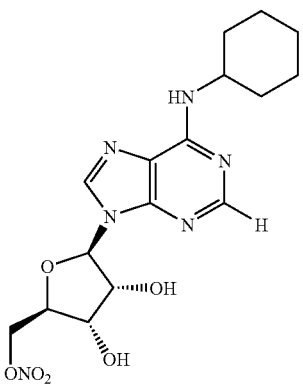

34

((2R,3S,4R,5R)-5-(6-(cyclohexylamino)-9H-purin-9-yl)-3,4-dihydroxytetrahydrofuran-2-yl)methyl nitrate, Compound F

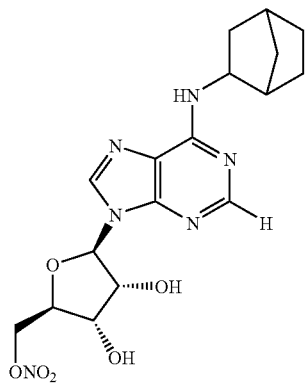

((2R,3S,4R,5R)-5-(6-(bicycle-[2.2.1]-heptan-2-ylamino)-9H-purin-9-yl)-3,4-dihydroxytetrahydrofuran-2-yl) methyl nitrate, Compound G

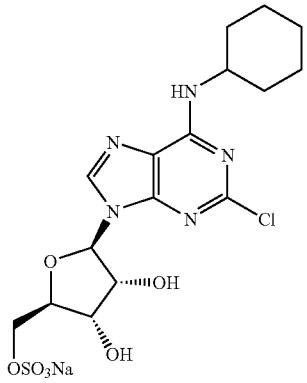

sodium ((2R,3S,4R,5R)-5-(2-chloro-6-(cyclohexylamino)-9H-purin-9-yl)-3,4-dihydroxytetrahydrofuran-2-yl)methyl sulfate, and Compound H

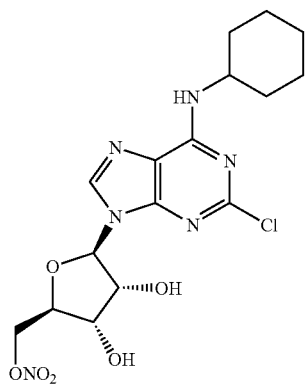

((2R,3S,4R,5R)-5-(2-chloro-6-(cyclohexylamino)-9H-purin-9-yl)-3,4-dihydroxytetrahydrofuran-2-yl)methyl nitrate, or pharmaceutically acceptable salts thereof.

4. The method as claimed in claim 3 wherein the compound is selected from the group consisting of ((2R,3S,4R,5R)-5-(6-(cyclopentylamino)-9H-purin-9-yl)-3,4-dihydroxytetrahydrofuran-2-yl)methyl nitrate; ((2R,3S,4R,5R)-5-(2-chloro-6-(cyclopentylamino)-9H-purin-9-yl)-3,4-dihydroxytetrahydrofuran-2-yl)methyl nitrate; sodium ((2R,3S,4R,5R)-5-(6-(cyclopentylamino)-9H-purin-9-yl)-3,4-dihydroxytetrahydrofuran-2-yl)methyl sulfate; and ((2R,3S,4R,5R)-3,4-dihydroxy-5-(6-(tetrahydrofuran-3-ylamino)-9H-purin-9-yl)tetrahydrofuran-2-yl)methyl nitrate.

5. The method as claimed in claim 1 further comprising applying about 0.05 mg/ml to about 7.0 mg/ml of the compound according to Formula I from 1 to 4 times daily.

6. The method as claimed in claim 1 further comprising applying about 20-700 µg of the compound according to Formula I from 1 to 2 times daily.

7. The method as claimed in claim 1 further comprising applying about 350 µg of the compound according to Formula I from 1 to 2 times daily.

8. The method as claimed in claim 5, wherein the compound is administered in drops.

9. The method of claim 8, wherein the compound is administered in 1 to 2 drops.

10. The method as claimed in claim 1 wherein the IOP of the affected eye is reduced by at least 10%.

11. The method as claimed in claim 1 wherein the IOP of the affected eye is reduced by about 10-20%.

12. The method as claimed in claim 1, wherein the IOP of the affected eye is reduced by 20% or more.

13. The method as claimed in claim 1 wherein the IOP of the affected eye is reduced by 10% for more than 3 hours.

14. The method as claimed in claim 1 wherein the IOP of the affected eye is reduced by about at least 10-20% for more than 3 hours.

15. The method as claimed in claim 1 wherein the IOP of the affected eye is reduced by 20% or more for more than 3 hours.

16. The method as claimed in claim 1, wherein the IOP of the affected eye is reduced by at least 10% for at least 6 hours.

17. The method as claimed in claim 1, further comprising prior, simultaneous or sequential, application of a second IOP reducing agent.

18. The method as claimed in claim 17 wherein the second IOP reducing agent is selected from the group comprising: β-blockers, prostaglandin analogs, carbonic anhydrase inhibitors, rho-kinase inhibitors, $\alpha_2$ agonists, miotics, neuroprotectants, $A_3$ antagonists, $A_{2A}$ agonists, ion channel modulators and combinations thereof.

19. A method of treating diseases and conditions caused by elevated IOP in a human subject in need thereof by administering an effective amount of a selective adenosine $A_1$ agonist to an affected eye of the subject wherein the agonist is a compound defined by formula I in claim 1.

20. The method of claim 19, wherein the diseases and conditions caused by elevated IOP in a human are selected from the group consisting of normal-tension glaucoma, ocular hypertension (OHT), and primary open-angle glaucoma (POAG).

21. The method as claimed in claim 19 wherein the selective $A_1$ agonist is a compound of formula

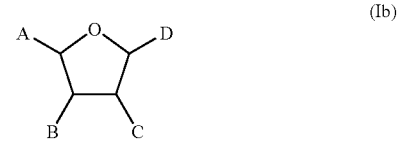

(Ib)

or a pharmaceutically acceptable salt thereof, wherein

A is —CH$_2$ONO$_2$;

B and C are —OH;

D is

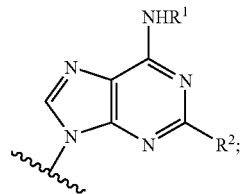

A and B are trans with respect to each other;

B and C are cis with respect to each other;

C and D are cis or trans with respect to each other;

$R^1$ is —C$_3$-C$_8$ monocyclic cycloalkyl, -3- to 7-membered monocyclic heterocyclyl or —C$_8$-C$_{12}$ bicyclic cycloalkyl; and $R^2$ is —H or -halo.

22. The method as claimed in claim 19 wherein the compound of Formula I is selected from the group consisting of:

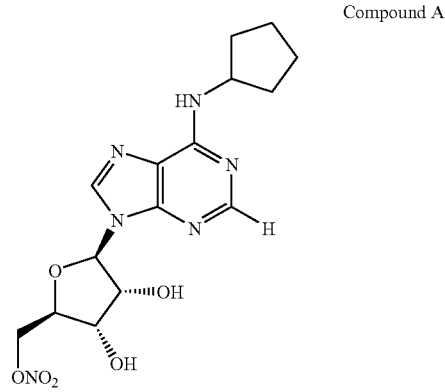

Compound A ((2R,3S,4R,5R)-5-(6-(cyclopentylamino)-9H-purin-9-yl)-3,4-dihydroxytetrahydrofuran-2-yl)methyl nitrate,

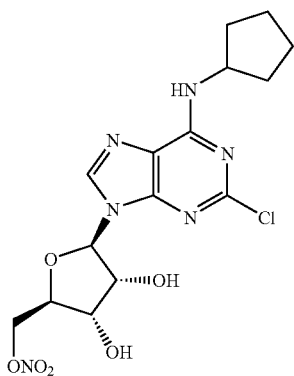

Compound B ((2R,3S,4R,5R)-5-(2-chloro-6-(cyclopentylamino)-9H-purin-9-yl)-3,4-dihydroxytetrahydrofuran-2-yl)methyl nitrate,

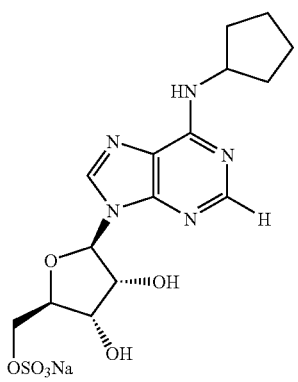

Compound C sodium ((2R,3S,4R,5R)-5-(6-(cyclopentylamino)-9H-purin-9-yl)-3,4-dihydroxytetrahydrofuran-2-yl)methyl sulfate,

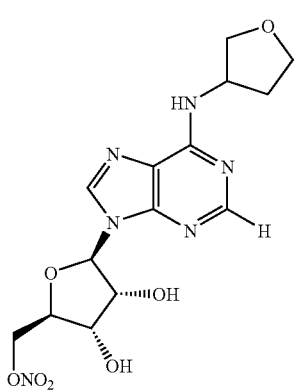

Compound D ((2R,3S,4R,5R)-3,4-dihydroxy-5-(6-(tetrahydrofuran-3-ylamino)-9H-purin-9-yl)tetrahydrofuran-2-yl)methyl nitrate,

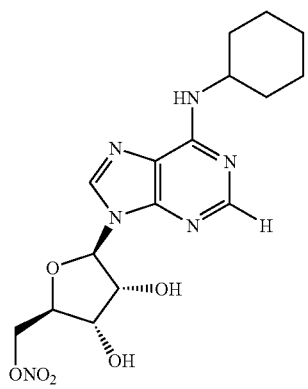

Compound E ((2R,3S,4R,5R)-5-(6-(cyclohexylamino)-9H-purin-9-yl)-3,4-dihydroxytetrahydrofuran-2-yl)methyl nitrate,

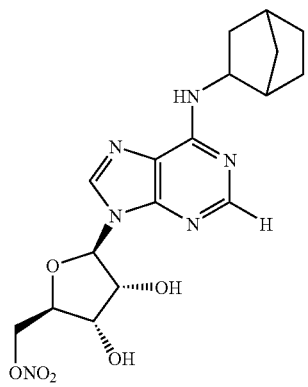

Compound F ((2R,3S,4R,5R)-5-(6-(bicycle-[2.2.1]-heptan-2-ylamino)-9H-purin-9-yl)-3,4-dihydroxytetrahydrofuran-2-yl) methyl nitrate,

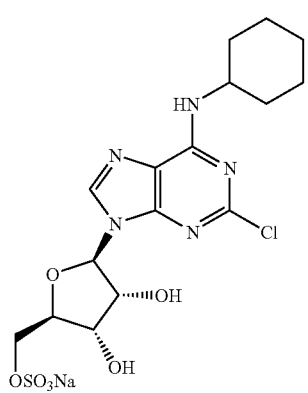

Compound G sodium ((2R,3S,4R,5R)-5-(2-chloro-6-(cyclohexylamino)-9H-purin-9-yl)-3,4-dihydroxytetrahydrofuran-2-yl)methyl sulfate, and

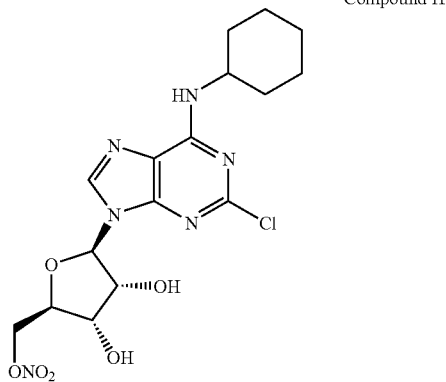

Compound H ((2R,3S,4R,5R)-5-(2-chloro-6-(cyclohexylamino)-9H-purin-9-yl)-3,4-dihydroxytetrahydrofuran-2-yl)methyl nitrate, or pharmaceutically acceptable salts thereof.

23. The method as claimed in claim 19 wherein the selective adenosine $A_1$ agonist is selected from the group consisting of:
   ((2R,3S,4R,5R)-5-(6-(cyclopentylamino)-9H-purin-9-yl)-3,4-dihydroxytetrahydrofuran-2-yl)methyl nitrate;
   ((2R,3S,4R,5R)-5-(2-chloro-6-(cyclopentylamino)-9H-purin-9-yl)-3,4-dihydroxytetrahydrofuran-2-yl)methyl nitrate;
   sodium ((2R,3S,4R,5R)-5-(6-(cyclopentylamino)-9H-purin-9-yl)-3,4-dihydroxytetrahydrofuran-2-yl)methyl sulfate; and
   ((2R,3S,4R,5R)-3,4-dihydroxy-5-(6-(tetrahydrofuran-3-ylamino)-9H-purin-9-yl)tetrahydrofuran-2-yl)methyl nitrate.

24. The method as claimed in claim 19 wherein the IOP of the affected eye is reduced by at least 10%.

25. The method as claimed in claim 19 wherein the IOP of the affected eye is reduced by about 10-20%.

26. The method as claimed in claim 19 wherein the IOP of the affected eye is reduced by 20% or more.

27. The method as claimed in claim 19 wherein the IOP of the affected eye is reduced by at least 10% for more than 3 hours.

28. The method as claimed in claim 19 wherein the IOP of the affected eye is reduced by about 10-20% for more than 3 hours.

29. The method as claimed in claim 19 wherein the IOP of the affected eye is reduced by 20% or more for more than 3 hours.

30. The method as claimed in claim 19 wherein the IOP of the affected eye is reduced by at least 10% for at least 6 hours.

31. The method as claimed in claim 19 wherein the effective amount of the selective adenosine $A_1$ agonist is at least 20 μg.

32. The method as claimed in claim 19 wherein the effective amount of the selective adenosine $A_1$ agonist is between 60 μg and 350 μg.

33. The method as claimed in claim 19 wherein the effective amount of the selective adenosine $A_1$ agonist is administered as a single dose.

34. The method as claimed in claim 19 wherein the effective amount of the selective adenosine $A_1$ agonist is administered as a twice daily dose.

35. An ophthalmic pharmaceutical composition comprising a compound of Formula I as defined in claim 1 and a pharmaceutically acceptable vehicle or excipient.

36. The pharmaceutical composition of claim 35, wherein the pharmaceutically acceptable vehicle or excipient is selected from the group consisting of: ophthalmologically acceptable preservatives, surfactants, viscosity enhancers, penetration enhancers, gelling agents, hydrophobic bases, vehicles, buffers, sodium chloride, and water, or any combination thereof.

37. The composition of claim 35 wherein said composition comprises from about 0.05 mg/ml to about 7 mg/ml of said compound of Formula I.

38. The composition of claim 35 wherein said composition comprises from about 0.4 mg/ml to about 7 mg/ml of said compound of Formula I.

39. The composition of claim 35 wherein the compound of Formula I is selected from the group consisting of: ((2R,3S,4R,5R)-5-(6-(cyclopentylamino)-9H-purin-9-yl)-3,4-dihydroxytetrahydrofuran-2-yl)methyl nitrate; ((2R,3S,4R,5R)-5-(2-chloro-6-(cyclopentylamino)-9H-purin-9-yl)-3,4-dihydroxytetrahydrofuran-2-yl)methyl nitrate; sodium ((2R,3S,4R,5R)-5-(6-(cyclopentylamino)-9H-purin-9-yl)-3,4-dihydroxytetrahydrofuran-2-yl)methyl sulfate; ((2R,3S,4R,5R)-3,4-dihydroxy-5-(6-(tetrahydrofuran-3-ylamino)-9H-purin-9-yl)tetrahydrofuran-2-yl)methyl nitrate; ((2R,3S,4R,5R)-5-(6-(cyclohexylamino)-9H-purin-9-yl)-3,4-dihydroxytetrahydrofuran-2-yl)methyl nitrate; ((2R,3S,4R,5R)-5-(6-(bicycle-[2.2.1]-heptan-2-ylamino)-9H-purin-9-yl)-3,4-dihydroxytetrahydrofuran-2-yl)methyl nitrate; sodium ((2R,3S,4R,5R)-5-(2-chloro-6-(cyclohexylamino)-9H-purin-9-yl)-3,4-dihydroxytetrahydrofuran-2-yl)methyl sulfate; and ((2R,3S,4R,5R)-5-(2-chloro-6-(cyclohexylamino)-9H-purin-9-yl)-3,4-dihydroxytetrahydrofuran-2-yl)methyl nitrate.

40. The composition of claim 35 wherein the compound is selected from the group consisting of ((2R,3S,4R,5R)-5-(6-(cyclopentylamino)-9H-purin-9-yl)-3,4-dihydroxytetrahydrofuran-2-yl)methyl nitrate; ((2R,3S,4R,5R)-5-(2-chloro-6-(cyclopentylamino)-9H-purin-9-yl)-3,4-dihydroxytetrahydrofuran-2-yl)methyl nitrate; sodium ((2R,3S,4R,5R)-5-(6-(cyclopentylamino)-9H-purin-9-yl)-3,4-dihydroxytetrahydrofuran-2-yl)methyl sulfate; and ((2R,3S,4R,5R)-3,4-dihydroxy-5-(6-(tetrahydrofuran-3-ylamino)-9H-purin-9-yl)tetrahydrofuran-2-yl)methyl nitrate.

41. An ophthalmic pharmaceutical composition comprising 0.05 mg/ml to about 7 mg/ml of a compound of Formula I as defined in claim 1, and a pharmaceutically acceptable carrier consisting of, from 1 mg/ml to about 140 mg/ml of hydroxypropyl β-cyclodextrin in saline for injection.

42. The ophthalmic pharmaceutical composition as claimed in claim 41 comprising 7 mg/ml of a compound of Formula I selected from the group consisting of: ((2R,3S,4R,5R)-5-(2-chloro-6-(cyclopentylamino)-9H-purin-9-yl)-3,4-dihydroxytetrahydrofuran-2-yl)methyl nitrate; sodium ((2R,3S,4R,5R)-5-(6-(cyclopentylamino)-9H-purin-9-yl)-3,4-dihydroxytetrahydrofuran-2-yl)methyl sulfate; and ((2R,3S,4R,5R)-3,4-dihydroxy-5-(6-(tetrahydrofuran-3-ylamino)-9H-purin-9-yl)tetrahydrofuran-2-yl)methyl nitrate.

* * * * *

UNITED STATES PATENT AND TRADEMARK OFFICE
CERTIFICATE OF CORRECTION

PATENT NO. : 8,470,800 B2  
APPLICATION NO. : 12/771289  
DATED : June 25, 2013  
INVENTOR(S) : Shikha Barman et al.

Page 1 of 1

It is certified that error appears in the above-identified patent and that said Letters Patent is hereby corrected as shown below:

In the Claims

Column 30, line 64 (Claim 1, line 30) "8 to 12-membered" should be "-8- to 12-membered"

Column 30, line 65 (Claim 1, line 31) "$C_3$-$C_8$ monocyclic cycloalkyl" should be "-$C_3$-$C_8$ monocyclic cycloalkyl"

Column 35, line 42 (Claim 13, line 2) after "reduced by" insert --at least--

Column 35, line 44 (Claim 14, line 2) after "about" delete "at least"

Signed and Sealed this  
First Day of July, 2014

Michelle K. Lee  
*Deputy Director of the United States Patent and Trademark Office*